(12) United States Patent
Ichiki

(10) Patent No.: US 11,087,461 B2
(45) Date of Patent: Aug. 10, 2021

(54) IMAGE PROCESSING DEVICE, IMAGE PROCESSING METHOD, MEDICAL IMAGING SYSTEM

(71) Applicant: SONY CORPORATION, Tokyo (JP)

(72) Inventor: Hiroshi Ichiki, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 150 days.

(21) Appl. No.: 16/303,242

(22) PCT Filed: Jun. 14, 2017

(86) PCT No.: PCT/JP2017/021949
§ 371 (c)(1),
(2) Date: Nov. 20, 2018

(87) PCT Pub. No.: WO2018/003503
PCT Pub. Date: Jan. 4, 2018

(65) Prior Publication Data
US 2019/0206053 A1    Jul. 4, 2019

(30) Foreign Application Priority Data
Jun. 28, 2016 (JP) .............................. JP2016-127687

(51) Int. Cl.
*G06K 9/00* (2006.01)
*G06T 7/00* (2017.01)
(Continued)

(52) U.S. Cl.
CPC ........ *G06T 7/0012* (2013.01); *A61B 1/00045* (2013.01); *A61B 1/045* (2013.01);
(Continued)

(58) Field of Classification Search
CPC .......... G02B 23/24; G06T 2207/10068; G06T 2207/20081; G06T 2207/20084; G06T 5/003; G06T 7/0012
See application file for complete search history.

(56) References Cited

U.S. PATENT DOCUMENTS 8,150,201 B2 * 4/2012 Kasai .................. H04N 5/2355
382/274
2007/0263942 A1 * 11/2007 Hirose .................... G06T 5/005
382/275
(Continued)

FOREIGN PATENT DOCUMENTS

CN        101351149 A     1/2009
CN        102596001 A     7/2012
(Continued)

OTHER PUBLICATIONS

International Search Report dated Sep. 5, 2017 in PCT/JP2017/021949, citing documents AO-AQ therein, 2 pages.
(Continued)

*Primary Examiner* — Avinash Yentrapati
(74) *Attorney, Agent, or Firm* — Xsensus LLP

(57) ABSTRACT

The present disclosure relates to an image processing device, and an image processing method that enable display of an endoscopic image in an easy-to-view manner, and a medical imaging system.

The image imaged by an endoscope device is smoothed by LPF and lightness I, chromaticity r, g, and brightness Y are obtained from a smoothed image. A histogram is obtained in units of blocks using the brightness Y, and a frequency in a direction being an upper order is obtained as a gradient bias feature amount Bb. Furthermore, the lightness and the chromaticity are also obtained as feature amounts Ib, rb and gb of lightness and chromaticity in units of blocks. Then, on the basis of a four-dimensional feature amount including Ib, (Continued)

rb and gb, Bb, a region of a subject in an image is classified into a surgical tool, gauze, or the like by a classifier, a region not classified into any of them is recognized as a biological tissue, and AE, AF, and blur correction are performed only with information of the region recognized as the biological tissue. The present disclosure can be applied to an endoscope system, a microscope system, and the like.

16 Claims, 15 Drawing Sheets

(51) Int. Cl.
*A61B 1/045* (2006.01)
*G02B 23/24* (2006.01)
*A61B 1/00* (2006.01)
*G06T 5/00* (2006.01)

(52) U.S. Cl.
CPC .............. *G02B 23/24* (2013.01); *G06T 5/003* (2013.01); *G06T 2207/10068* (2013.01); *G06T 2207/20081* (2013.01); *G06T 2207/20084* (2013.01)

(56) References Cited

U.S. PATENT DOCUMENTS

| | | | |
|---|---|---|---|
| 2011/0176726 A1* | 7/2011 | Lee | H04N 1/40012 382/163 |
| 2011/0182477 A1* | 7/2011 | Tamrakar | G06T 7/44 382/110 |
| 2013/0051680 A1* | 2/2013 | Kono | G06T 7/11 382/195 |
| 2013/0259372 A1* | 10/2013 | Xu | G06K 9/00624 382/170 |
| 2014/0005477 A1* | 1/2014 | Gupta | A61B 1/303 600/109 |
| 2015/0254848 A1* | 9/2015 | Ozaki | G06T 7/0012 382/128 |
| 2015/0294174 A1* | 10/2015 | Karkowski | G06F 16/5838 382/182 |
| 2015/0339817 A1* | 11/2015 | Kuriyama | G06T 7/64 348/71 |
| 2016/0253801 A1* | 9/2016 | Linard | G06T 7/174 382/128 |
| 2018/0322672 A1* | 11/2018 | Shibata | G06T 5/007 |

FOREIGN PATENT DOCUMENTS

| | | |
|---|---|---|
| CN | 103561629 A | 5/2014 |
| CN | 103971361 A | 8/2014 |
| CN | 104854620 A | 8/2015 |
| CN | 105612554 A | 5/2016 |
| JP | H06163191 A | 6/1994 |
| JP | 7-284090 A | 10/1995 |
| JP | 2014-166298 A | 9/2014 |
| JP | 2016-7273 A | 1/2016 |
| WO | WO 2015/052351 A1 | 4/2015 |

OTHER PUBLICATIONS

Li Wosong, Image classification algorithm analysis. "Chinese technology enterprise", No. 16, Aug. 15, 2007, p. 109+ 120.
Sebastian Bodenstedi et al., Superpixel-based Structure Classification for Laparoscopic Surgery. "Medical Imaging 2016; Image Guided Procedures, Robotic Interventions, and Modeling", Jun. 19, 2016, vol. 978618-1-978618-6.

* cited by examiner

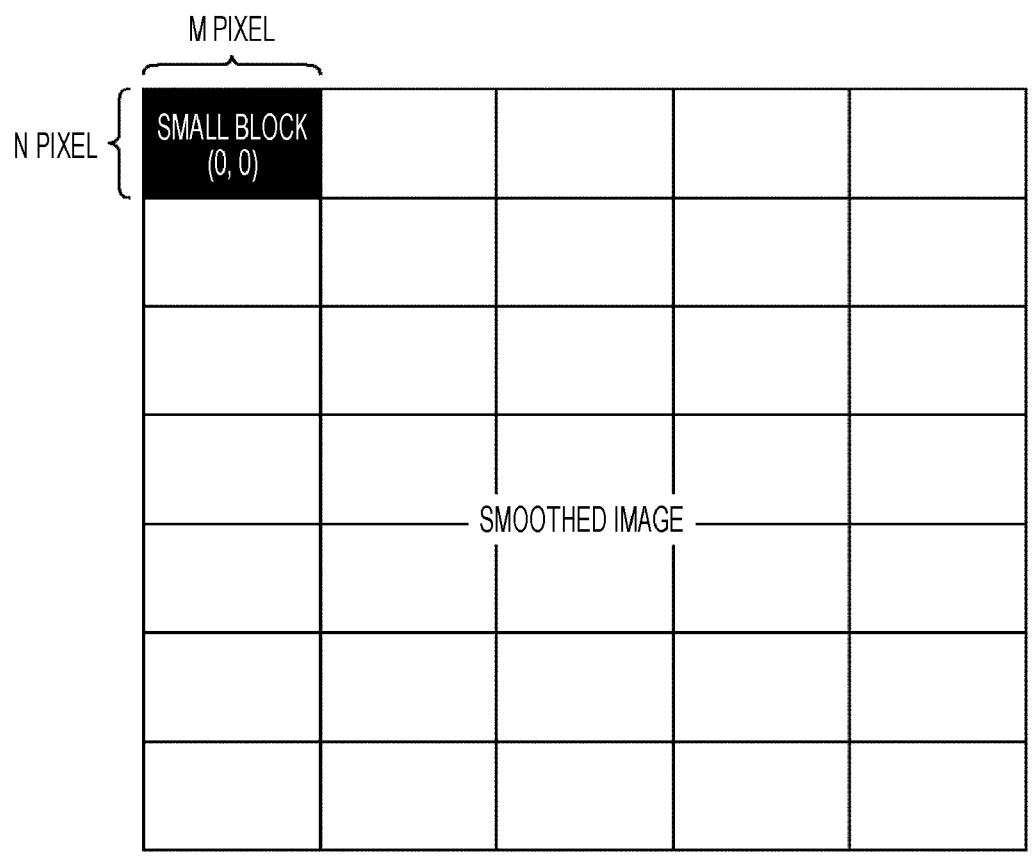

IMAGE PROCESSING DEVICE, IMAGE PROCESSING METHOD, MEDICAL IMAGING SYSTEM

TECHNICAL FIELD

The present disclosure relates to an image processing device, an image processing method, and a medical imaging system, and more particularly, to an image processing device, and an image processing method, capable of making an image in an endoscope device or the like easy to view by an operator, and a medical imaging system.

BACKGROUND ART

Endoscopic surgery performed while an endoscopic image imaged by an endoscope device is viewed has become widespread in general.

Since an image imaged by an endoscope device is an image imaged under a special environment, there is a growing need by an operator who performs surgery for images that are easy to view.

In view of this, in recent years, a technique has been proposed in which endoscopic images are analyzed, portions that are difficult to extract by binarization or three-dimensional display alone are classified, and displaying the portions visually easily understandable (see Patent Document 1).

CITATION LIST

Patent Document

Patent Document 1: Japanese Patent Application Laid-Open No. 7-284090

SUMMARY OF THE INVENTION

Problems to be Solved by the Invention

By the way, since an endoscopic image imaged by an endoscope device is an image imaged under a special environment as compared with general imaging, in some cases, appropriate processing cannot be performed when auto exposure (AE) or auto focus (AF) is performed by using an endoscopic image, for example.

In other words, in an endoscopic image, a metallic surgical tool, gauze, a wall surface including a biological tissue in a body, or the like is a light reflecting object, and for example, a phenomenon such as whitening occurs, so that there is a concern that AE and AF cannot be appropriately realized.

Furthermore, in a case where an item such as a surgical tool, a thread, a needle, an organ, or a finger is included in an image, there is a concern that AE and AF cannot be appropriately realized by the item frequently entering and exiting a displayed surgical field.

Moreover, a thread close to lighting, reflection, a scratch on a surgical tool, irregularities of a subject, or the like is detected as high brightness edge in some cases, and furthermore, low contrast is easy to occur in tissues such as fats, smoke, dirt on a lens or the like, so that there is a concern that AF cannot be appropriately realized in any cases.

Furthermore, similarly, a surgical tool, gauze, or the like in an endoscopic image causes a motion detection result unnecessary for blur correction, so that there is a concern that blur correction or the like cannot be appropriately realized.

The present disclosure has been made in view of such circumstances, and in particular, it is an object of the present invention to appropriately apply AE, AF, and blur correction to an endoscopic image so that an endoscopic image that is easy to view by an operator can be presented.

Solutions to Problems

An image processing device according to an aspect of the present disclosure is an image processing device including: a smoothing unit that smooths a biological image generated by imaging an inside of a biological body including a biological tissue by a medical imaging device; and a classification unit that classifies each subject included in each region in the biological image on the basis of a smoothed image obtained by smoothing the biological image by the smoothing unit.

The classification unit may classify each subject included in each region into the biological tissue or one other than the biological tissue on the basis of the smoothed image.

The classification unit may classify each subject included in each region on the basis of lightness, chromaticity, and brightness of the smoothed image.

The image processing device may further include: a conversion unit that converts a pixel value of each pixel of the smoothed image into lightness, chromaticity, and brightness; and a brightness gradient calculation unit that obtains a gradient direction and a gradient strength of the brightness of each pixel in the smoothed image. The classification unit may classify a subject in the biological image on the basis of the lightness, the chromaticity, and the gradient direction and the gradient strength, in units of blocks of a predetermined size in the biological image.

The block of a predetermined size may include a plurality of small blocks having a size smaller than the predetermined size, and further include a gradient bias calculation unit that obtains a moving addition of a histogram of a gradient strength in units of small blocks to obtain a histogram being the moving addition as a gradient bias feature amount in units of small blocks.

The gradient bias calculation unit may obtain a moving addition of a histogram of a gradient strength of a plurality of the small blocks in units of the blocks to calculate a gradient strength of higher order of a histogram being the moving addition as a gradient bias feature amount of a predetermined size, and the classification unit may classify a subject in the biological image on the basis of the lightness, the chromaticity, and the gradient bias feature amount of the block unit.

The gradient bias calculation unit may calculate a sum of gradient strength up to a predetermined higher order of the histogram being the moving addition as the gradient bias feature amount of the block unit of a predetermined size.

The classification unit may classify one other than the biological tissue into any of a surgical tool, gauze, an outside of a mask, a pool of blood, and a high brightness portion in the biological image.

The classification unit may classify each subject included in each region in the biological image into any of a surgical tool, gauze, an outside of a mask, a pool of blood, or a high brightness portion other than a biological tissue, and classify a subject in a region not classified as any type as a biological tissue.

The classification unit may include a classifier using a neural network.

The classification unit may include a classifier using machine learning using boosting.

The image processing device may further include an exposure adjustment unit that adjusts exposure in a medical imaging device on the basis of information regarding brightness of the region classified as the biological tissue in the biological image.

The image processing device may further include a focus adjustment unit that adjusts focus in a medical imaging device on the basis of only information of the region classified as the biological tissue in the biological image.

The image processing device may further include a blur correction unit that corrects blur in the biological image on the basis of information regarding moving of the region classified as the biological tissue in the biological image.

The image processing device may further include: an image processing unit that processes an image so as to hatch a position on the biological image corresponding to the type of the classified subject on the basis of the classification result of the classification unit; and a display control unit that controls display of the biological image processed by the image processing unit.

The image processing device may further include an operation unit that specifies a re-learning range requiring re-learning and specifies a correct label indicating a correct subject on the displayed biological image, and the classification unit may perform re-learning so as to classify a subject corresponding to the correct label in the re-learning range.

The biological image may be an endoscopic image imaged by an endoscope device.

An image processing method according to an aspect of the present disclosure includes a step of smoothing an image, smoothing a biological image generated by imaging an inside of a biological body including a biological tissue by a medical imaging device, and classifying each subject included in each region in the biological image on the basis of a smoothed image obtained by smoothing the biological image.

A medical imaging system according to an aspect of the present disclosure includes: an image processing device including a smoothing unit that smooths a biological image generated by imaging an inside of a biological body including a biological tissue by a medical imaging device, and a classification unit that classifies each subject included in each region in the biological image on the basis of a smoothed image obtained by smoothing the biological image by the smoothing unit; and a medical imaging device including an imaging unit that images the image.

In an aspect of the present disclosure, a biological image generated by imaging an inside of a biological body including a biological tissue by a medical imaging device is smoothed, and each subject included in each region in the biological image is classified on the basis of a smoothed image obtained by smoothing the biological image.

Effects of the Invention

According to an aspect of the present disclosure, it is possible to present an endoscopic image that is easy to view.

BRIEF DESCRIPTION OF DRAWINGS

FIG. 3 is a diagram illustrating an example of a BOX filter.

FIG. 4 is a diagram illustrating an example of obtaining a four-dimensional feature amount in unit of a small block.

MODE FOR CARRYING OUT THE INVENTION

Figure 1:
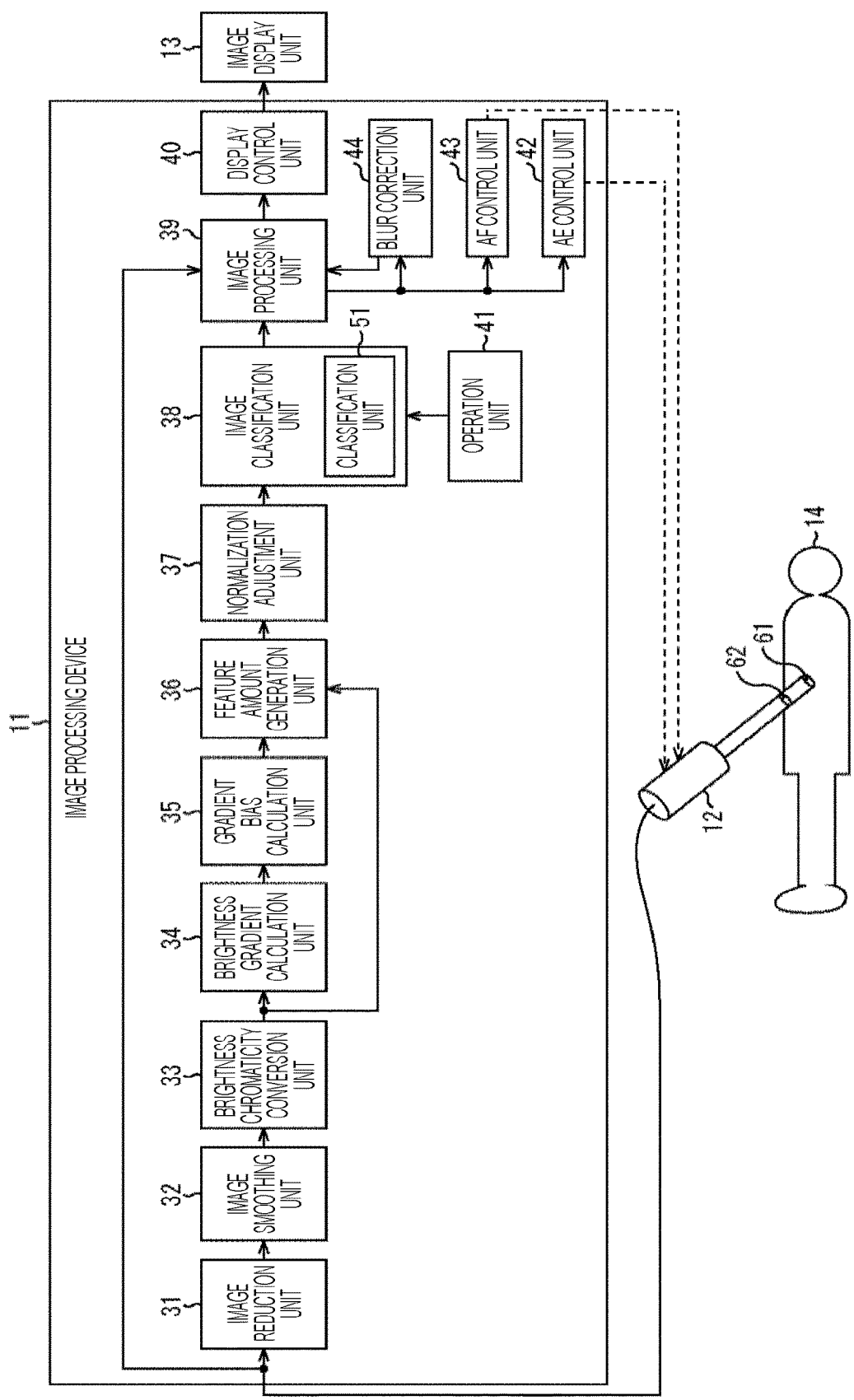
FIG. 1 is a diagram illustrating a configuration example of an endoscope system of the present disclosure.

Preferred embodiments of the present disclosure will be described in detail below with reference to the accompanying drawings. Note that, in the present specification and the drawings, the same reference numerals are given to the constituent elements having substantially the same functional configuration, and redundant explanations are omitted.

Furthermore, explanation will be given in the following order.

1. Overview of image processing device of present disclosure

2. Configuration example of endoscope system using image processing device of present disclosure 3. Application example 1. Overview of Image Processing Device of Present Disclosure In order to perform processing such as auto exposure (AE), auto focus (AF), and blur correction on the endoscopic image imaged by an endoscope device, processing suitable for features of the endoscopic image is required.

In other words, an endoscopic image imaged by the endoscope device is imaged in a very narrow space in which the distance between an imaging surface and a subject is relatively close and high intensity illumination is used.

For this reason, when a handle of a surgical tool, a cavity wall surface or the like is close to an illumination, or a light projection direction of the illumination is the imaging direction, if conditions such as that the cavity wall surface exists so as to directly face a front face, white gauze or the like is illuminated by a strong illumination, and the like are met, a phenomenon that the surgical tool, the cavity wall surface or the like strongly reflects illumination light occurs. As a result, a phenomenon so-called white skipping occurs, which makes it impossible to appropriately recognize lightness, making it impossible to properly function the AE.

Furthermore, since the contrast may become extremely strong in the local area of a cavity wall surface, a suture thread, a surgical tool, or the like, there may be cases where the part is in focus, so that the AF cannot function appropriately. Furthermore, when smoke or the like involved in use of an electric scalpel or the like is generated, low contrast of a subject occurs due to the smoke, and focusing cannot be performed in some cases, so that the AF cannot function appropriately in some cases as well.

Moreover, since a surgical tool and gauze move differently from an affected part requiring blur correction, unnecessary motion may be detected for blur correction and as a result, appropriate blur correction cannot be performed in some cases for imaging of an affected part that a doctor who is an operator desires to view.

Furthermore, when viewing an endoscopic image, a doctor who is an operator generally has a desire to view a biological tissue being an affected part in an endoscopic image that is a viewing target.

In view of such a requirement, generally, it is conceivable that an endoscopic image is subjected to enhancement processing or the like, a high image quality processing such that an affected part can be detected is performed, the affected part is detected by object detection and object identification, and AE, AF, and blur correction are performed.

Meanwhile, in order to display an endoscopic image in a state in which an endoscopic operation is being performed, it is necessary to present an endoscopic image with a low delay. However, performing the object detection and the object identification after applying the enhancement processing to the endoscopic image has a high operation processing load, and it is not practical to realize endoscopic image presentation with low delay.

In considering a technique for appropriately applying AE, AF, and blur correction to an endoscopic image while maintaining a low delay, first, it is necessary to select a parameter with a low processing load.

More specifically, as parameters of an endoscopic image that are likely to be used for adjustment in realizing AE, AF, and blur correction, for example, brightness information, chromaticity information, labeling (area/shape), contour model (Snake or the like), straight edge (HOUGH conversion or the like), pattern (HAA/LBP feature amount or the like), image tilt (gradient) (HOG feature amount or the like), histogram, texture, or the like are conceivable.

Among the above-described parameters, since labeling (area/shape), contour model (Snake or the like), straight edge (HOUGH transformation or the like), and pattern (HAA/LBP feature amount or the like) require sequential operation and repeated operation, the processing load is high, and thus, it cannot be said that those are parameters suitable for processing with respect to the endoscopic image. Furthermore, when a histogram is used while the size of a subject changes drastically, the processing load can increase. Furthermore, regarding textures, there are many images that are out of focus and it is often difficult to detect, so that there may be a delay for applying appropriate processing.

Thus, in the image processing device of the present disclosure, AE, AF, and blur correction are performed using brightness information with high interrelation property of AE, chromaticity information with a small amount of operation amount and capable of comparatively enhancing recognition performance by learning, and image tilt (gradient) that allows a surgical tool to be detected without being affected by focusing.

However, with these parameters, it is difficult to identify biological tissue with high accuracy. Thus, the image processing device of the present disclosure, instead of directly detecting and identifying a target biological tissue, detects and identifies regions other than biological tissue being a viewing target, such as a surgical tool, gauze, an outside of a mask, a pool of blood, and a high brightness region that are relatively easy to detect, and regards the other regions as regions of biological tissue being viewing target.

At this time, the image processing device of the present disclosure performs smoothing by applying low pass filter (LPF) to the endoscopic image imaged by the endoscope device, so that even when the endoscopic image is not focused, a bias is strongly imposed on image gradient with respect to a region other than biological tissue such as a surgical tool portion. Moreover, the image processing device according to the present disclosure extracts the bias of the image gradient as a feature amount, reduces the dimension of the feature amount, reduces the operation amount, reduces the processing load, and increases the processing accuracy, so that the biological tissue in the endoscopic image being the viewing target of the operator can be presented with low delay.

2. Configuration Example of Endoscope System Using Image Processing Device of Present Disclosure A configuration example of an endoscope system using the image processing device of the present disclosure will be described with reference to FIG. 1.

The endoscope system shown in FIG. 1 includes an image processing device 11, an endoscope device 12, and an image display unit 13. At a distal end portion of the endoscope device 12, an imaging element 62 is provided. In other words, in a state in which the distal end portion of the endoscope device 12 is inserted into the body of a patient 14, the endoscope device 12 images to obtain an endoscopic image inside the body and supplies the endoscopic image to the image processing device 11. The image processing device 11 processes the endoscopic image supplied from the endoscope device 12 and presents an endoscopic image that is easy to view by an operator.

More particularly, the endoscope device 12 is a rod-shaped device, and an image formed on the imaging element 62 by an optical block 61 including a plurality of lenses or the like provided at a distal end portion of the endoscope device 12 is imaged by the imaging element 62.

More specifically, for example, the endoscope device 12 images an image inside the body as an endoscopic image, and outputs the image to the image processing device 11 as a high-resolution image such as a 2K image (for example, about 1920×1080), a 4K image (for example, about 4096× 2160 or about 3840×2160), or an 8K image (for example, about 7680×4320).

Note that, although not shown, the imaging element 62 is provided with a signal processing unit, predetermined signal processing is performed, an image is generated, and the generated image is output. Furthermore, the resolution of the image imaged by the endoscope device 12 is preferable also for images of other resolutions. Furthermore, in the present embodiment, unless otherwise noted, the explanation will be made assuming that the endoscopic image captured by the endoscope device 12 is a 4K image.

The image processing device 11 processes the endoscopic image of the inside of the body of the patient 14 supplied from the endoscope device 12 and presents an endoscopic image that is easy for the operator to view.

More particularly, the image processing device 11 includes an image reduction unit 31, an image smoothing unit 32, a brightness chromaticity conversion unit 33, a brightness gradient calculation unit 34, a gradient bias calculation unit 35, a feature amount generation unit 36, a normalization adjustment unit 37, an image classification unit 38, an image processing unit 39, a display control unit 40, an operation unit 41, an auto exposure (AE) control unit 42, an auto focus (AF) control unit 43, and a blur correction unit 44.

The image reduction unit 31 reduces the input image having high resolution including, for example, a 4K image imaged by the endoscope device 12 into an image having resolution of, for example, about 1024×540, and supplies the reduced image to the image smoothing unit 32.

The image smoothing unit 32 smooths the image reduced by the image reduction unit 31 by, for example, applying low pass filter (LPF), converts the image into an image of which image gradient is easy to acquire, and supplies the converted image to the brightness chromaticity conversion unit 33 by the processing described later.

The brightness chromaticity conversion unit 33 converts values of each pixel to lightness I, brightness Y, and chromaticity r, g, on the basis of a smoothed image, and supplies the converted value to the brightness gradient calculation unit 34 and the feature amount generation unit 36.

The brightness gradient calculation unit 34 calculates a direction of gradient (tilt direction) and the gradient strength of each pixel by applying the Sobel operator, generates a histogram Hsb in the tilt direction, which is loaded with the calculated gradient strength, and supplies the histogram Hsb to the gradient bias calculation unit 35.

The gradient bias calculation unit 35 moves and adds the histogram Hsb in the tilt direction obtained in units of small blocks to obtain a histogram Hb loaded with gradient strength in the tilt direction in units of blocks including a plurality of small blocks. Moreover, the gradient bias calculation unit 35 adds the gradient strength (tilt strength) loaded with the gradient strength up to the second order using the histogram Hb in units of blocks, and supplies the added gradient strength to the feature amount generation unit 36 as the gradient bias feature amount Bb in units of blocks.

The feature amount generation unit 36 operates the lightness Isb and the chromaticity rsb and gsb in units of small blocks described above. Furthermore, the feature amount generation unit 36 operates the lightness Ib and the chromaticity rb and gb in units of blocks including a plurality of small blocks from the lightness Isb and the chromaticity rsb and gsb in units of small blocks. Furthermore, the feature amount generation unit 36 forms a four-dimensional feature amount together with the gradient bias feature amount Bb, the brightness Ib, and the chromaticity rb and gb in units of blocks, and supplies the four-dimensional feature amount to the normalization adjustment unit 37.

The normalization adjustment unit 37 normalizes and adjusts the four-dimensional feature amount, and supplies the normalized amount to the image classification unit 38.

The image classification unit 38 includes a classifier 51 that classifies the subject in the image on the basis of the four-dimensional feature amount, classifies the subject in the image by the classifier 51 on the basis of the four-dimensional feature amount, and supplies the classification result to the image processing unit 39. Furthermore, in a case where there is an error in the image classification in the displayed image, the image classification unit 38 accepts an input of a label or the like for re-learning in accordance with the operation of the user, supplies the input to the classifier 51, and causes re-learning.

The image processing unit 39 applies image processing in accordance with the classification result supplied from the image classification unit 38 to the image supplied from the endoscope device 12, supplies the processed image to the display control unit 40, and supplies the processed image to the AE control unit 42, the AF control unit 43, and the blur correction unit 44. The display control unit 40 controls the image display unit 13 including a liquid crystal display (LCD) or the like to display the supplied image as an endoscopic image.

In other words, for example, the image classification unit 38 classifies a surgical tool, gauze, an outside of a mask, a pool of blood, and a high brightness portion in the image in a predetermined unit of block in the image, for example. Thus, the image processing unit 39 explicitly displays that regions corresponding to each classification result are out of the viewing targets on the basis of the classification result, by hatching the regions by different colors for each corresponding target, or the like. Furthermore, as a result, the regions not hatched are displayed as images of only biological tissue.

The AE control unit 42 appropriately controls the lightness on the basis of the image of the region of only biological tissue in the endoscopic image, and controls the AE of the imaging element 62 including a complementary metal oxide semiconductor (CMOS) image sensor or the like, for example, in the endoscope device 12. With this control, appropriate AE is realized. Note that, processing indicated by the dotted lines from the AE control unit 42 to the imaging element 62 in FIG. 1 is realized in reality, for example, by similar wiring as a transmission cable for transmitting the endoscopic image from the endoscope device 12 to the image processing device 11.

The AF control unit 43 controls an optical block 61 including a plurality of lenses or the like so that an incident light is focused on the imaging element 62 appropriately in the endoscope device 12 on the basis of the image in the region of only biological tissue among the endoscopic images, to control the AF. With this control, appropriate AF is realized. Note that, processing indicated by the dotted lines from the AF control unit 43 to the optical block 61 in FIG. 1 is realized in reality, for example, by similar wiring as a transmission cable for transmitting the endoscopic image from the endoscope device 12 to the image processing device 11.

The blur correction unit 44 detects motion on the basis of the image in the region of only biological tissue among the endoscopic images and controls the blur correction in accordance with the detected motion. With this correction, appropriate blur correction is realized.

Display Processing

Figure 2:
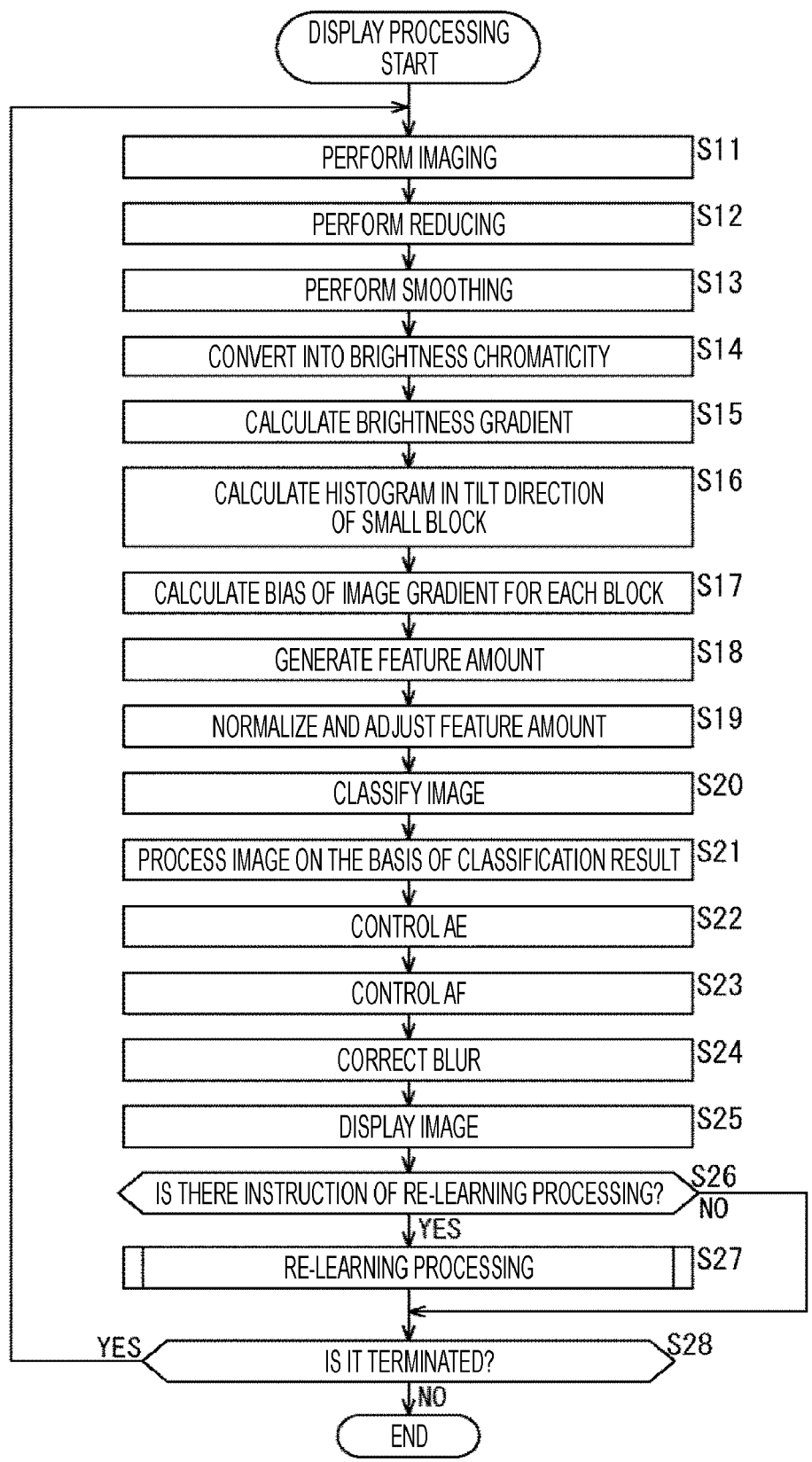
FIG. 2 is a flowchart illustrating display processing by the endoscope system of FIG. 1.

Next, display processing by the endoscope system will be described with reference to the flowchart of FIG. 2.

In step S11, the imaging element 62 of the endoscope device 12 images an image formed by the optical block 61 as an endoscopic image including a 4K image, for example, and supplies the endoscopic image to the image processing device 11.

More particularly, the imaging element 62 applies simple development processing on an imaged RAW image, or uses an RGB image that has already been subjected to development processing, as it is. Furthermore, in a case where development processing is required, in the case of an image sensor of a Bayer structure, the imaging element 62 applies demosaic processing, gain adjustment and white balance processing, defective pixel correction, color correction by a linear matrix, clip processing for accommodating a value of a signal within a valid range, and gamma correction.

In step S12, the image reduction unit 31 reduces the endoscopic image imaged by the endoscope device 12. More particularly, in the smoothing processing of the latter stage, if LPF including a BOX filter having large number of taps is directly applied to the 4K image, the operation amount increases, and therefore, the image reduction unit 31 reduces the endoscopic image including a 4K image into an image having resolution of 1024×540, for example, and supplies the reduced image to the image smoothing unit 32.

In step S13, the image smoothing unit 32 applies the LPF including a BOX filter of a predetermined size to each pixel of the endoscopic image, smooths the endoscopic image, and supplies the smoothed image to the brightness chromaticity conversion unit 33. For example, the BOX filter is a filter as shown in FIG. 3, and in a case of FIG. 3, an example of a filter of 5 pixels×5 pixels is shown. With respect to a pixel of interest in the colored center in the drawing, each pixel in 5 pixels×5 pixels in the periphery of the pixel of interest is multiplied by a coefficient $1/25$ and the product sum thereof is obtained, so that the image is smoothed.

In step S14, the brightness chromaticity conversion unit 33 converts the pixel value of each pixel of the smoothed endoscopic image into lightness, chromaticity, and brightness, supplies the brightness to the brightness gradient calculation unit 34, and supplies the lightness and the chromaticity to the feature amount generation unit 36.

More particularly, the brightness chromaticity conversion unit 33 converts the pixel value into lightness, chromaticity, and brightness, for example, by operating the following expressions (1) to (4) using the pixel value RGB in the pixel (x, y).

[Math. 1]
$$I(x,y) = R + G + B \quad (1)$$

[Math. 2]
$$r(x,y) = R/(R+G+B) \quad (2)$$

[Math. 3]
$$g(x,y) = G/(R+G+B) \quad (3)$$

[Math. 4]
$$Y(x,y) = 0.299 \times R + 0.587 \times G + 0.114 \times B \quad (4)$$

Here, the RGB is the pixel value of red, green, and blue, the I(x,y) of the pixel (x,y) is lightness, r(x,y), g(x,y) are chromaticity, and Y(x y) is brightness.

In step S15, the brightness gradient calculation unit 34 calculates the gradient direction and the gradient strength in units of pixels using the brightness Y for each pixel, and supplies the calculated gradient direction and the gradient strength to the gradient bias calculation unit 35.

More specifically, the brightness gradient calculation unit 34 applies Sobel operator of coefficients represented by the following expressions (5) and (6).

[Math. 5]
$$S_x = \begin{bmatrix} -1 & 0 & 1 \\ -2 & 0 & 2 \\ -1 & 0 & 1 \end{bmatrix} \quad (5)$$

[Math. 6]
$$S_x = \begin{bmatrix} -1 & -2 & -1 \\ 0 & 0 & 0 \\ 1 & 2 & 1 \end{bmatrix} \quad (6)$$

Here, Sx and Sy are brightness obtained by multiplying the brightness Y of the pixel in the coordinates (x,y) by the Sobel operator of the expressions (5) and (6), respectively.

Moreover, the brightness gradient calculation unit 34 operates the gradient (tilt) direction ang(x,y) of each pixel (x,y) and the gradient strength g (x,y) by the operation represented by the following expressions (7) and (8).

[Math. 7]
$$g(x, y) = \sqrt{fx(x, y)^2 + fy(x, y)^2} \quad (7)$$

[Math. 8]
$$d(x, y) = \tan^{-1}\left(\frac{fy(x, y)}{fx(x, y)}\right), ang(x, y) \quad (8)$$
$$= (d(x, y) + \pi) \times \frac{BIN - 1}{2\pi}$$

Here, fx(x,y) and fy(x,y) are Sx(x,y) and Sy(x,y), respectively, that are obtained by multiplying the pixel of the coordinate (x,y) by the Sobel operator of expressions (5) and (6) described above. Furthermore, d(x,y) is the gradient (tilt) angle (radian), ang(x,y) is the gradient (tilt) direction allocated on the basis of the gradient angle d(x,y), and is a value rounded to integer precision. Moreover, BIN is the number of directions, for example, 12.

In step S16, the gradient bias calculation unit 35 calculates a histogram of the tilt direction loaded with the above-described gradient strength in units of small blocks.

More specifically, as shown in FIG. 4, the smoothed endoscopic image is divided into small blocks of, for example, M pixels×N pixels, and the following Expression (9) is operated for each small block.

[Math. 9]
$$Hsb(sx,sy)[ang(x,y)] += g(x,y)/M/N \quad (9)$$

Here, (sx,sy) represents the coordinate of the small block. Hsb(sx,sy) is a feature amount including the histogram of the gradient direction ang(x,y) weighted by the gradient strength g(x,y) in units of small blocks. In other words, Expression (9) represents that a histogram is generated as a result by individually calculating the frequency of the gradient direction ang(x,y) weighted by the gradient strength g (x,y), and the set of the histograms itself is the feature amount. This feature amount is generally called the histogram of oriented gradients (HOG).

Note that, as described above, in a case where the endoscopic image has a resolution of 1024×540, for example, if M=8 and N=6 are satisfied, the endoscopic image is divided into 128×90 small blocks, for example.

In step S17, the gradient bias calculation unit 35 calculates the gradient bias feature amount Bb by using the histogram Hsb(sx,sy) of the gradient direction loaded with the gradient strength in units of small blocks, in units of block including a plurality of small blocks, and supplies the calculation result to the feature amount generation unit 36.

Figure 5:
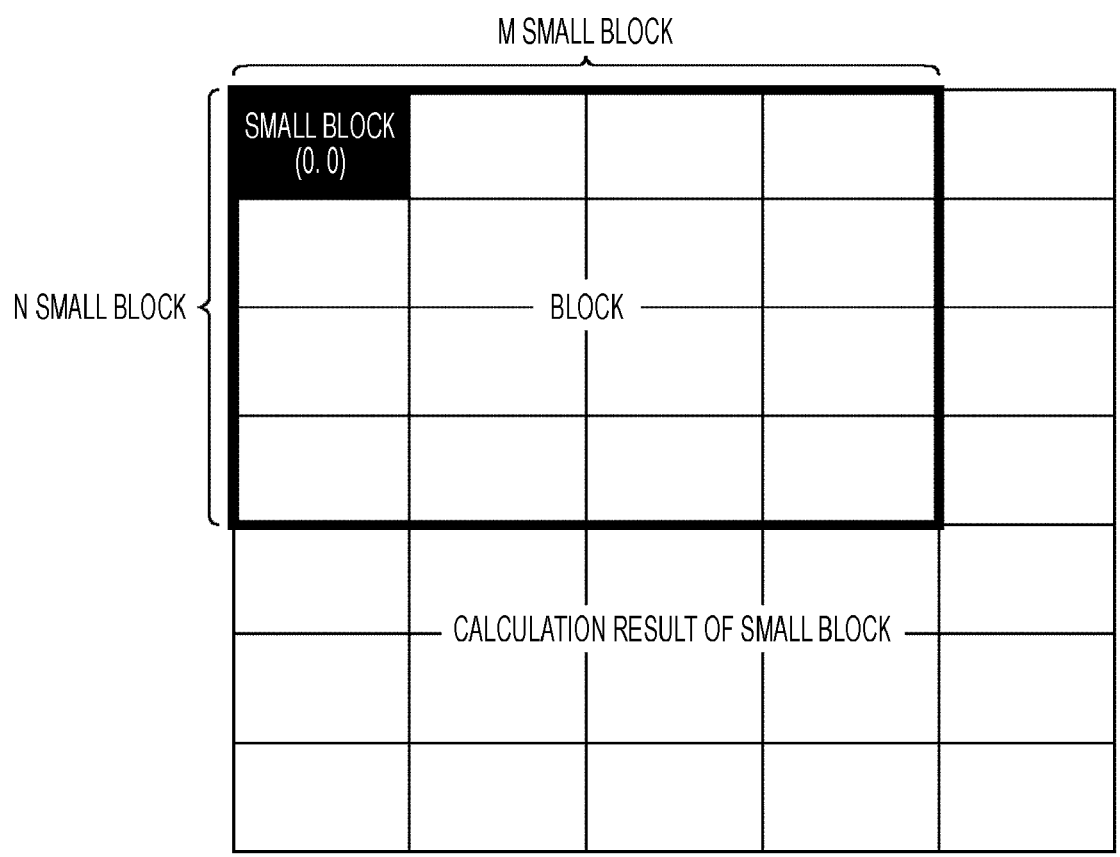
FIG. 5 is a diagram illustrating an example of obtaining a four-dimensional feature amount in unit of a block.

More specifically, as indicated by the thick line frame in FIG. 5, the smoothed endoscopic image is for example, divided into blocks of M small blocks×N small blocks, and the following Expression (10) is operated for each block.

[Math. 10]

$$Hb(bx, by) = \frac{1}{M \times N} \sum_{i=0}^{M} \sum_{j=0}^{N} Hsb(bx + i, by + j) \qquad (10)$$

Here, (bx,by) represents the coordinate of the block. Hb(bx,by) is a feature amount including a histogram of the gradient direction loaded with the gradient strength and is a result of addition of the gradient strength of each gradient direction.

Moreover, the gradient bias calculation unit 35 calculates the gradient bias feature amount Bb by operating the following Expression (11) on the basis of the histogram Hb(bx,by) of the gradient strength in units of blocks.

[Math. 11]

$$Bb(bx,by)=\max1(bx,by)+\max2(bx,by) \qquad (11)$$

Here, Bb is a gradient bias feature amount, and max Q(bx,by) represents the Q order of the histogram of the gradient strength of the block (bx,by). In other words, in Expression (11), the sum of the gradient strength up to the second order is substantially the gradient bias feature amount Bb for each block.

Figure 6:
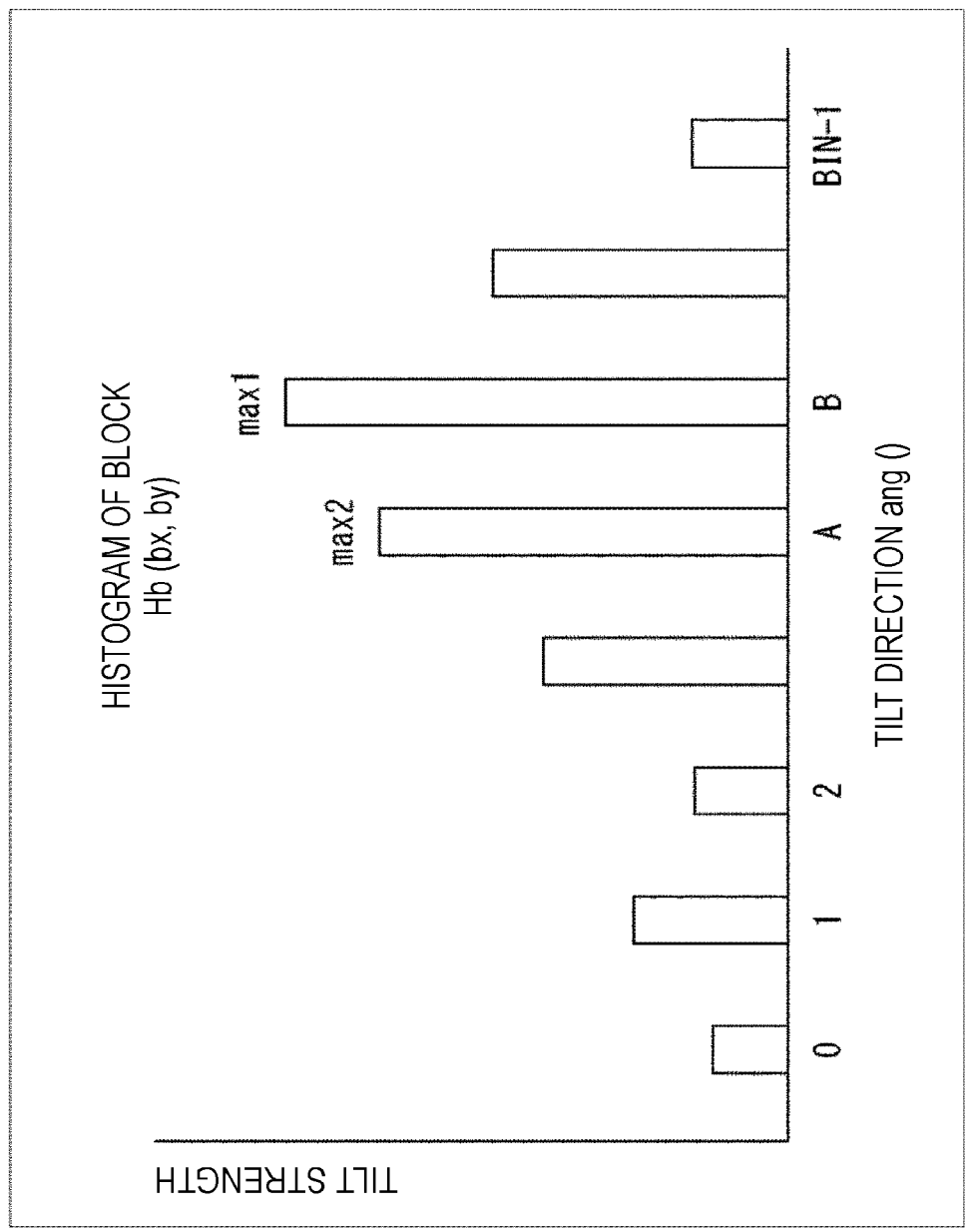
FIG. 6 is a diagram illustrating an example of obtaining a gradient bias feature amount in unit of a block.

In a predetermined block, for example, in a case where the histogram of the gradient strength as shown in FIG. 6 is desired, the sum of the gradient strength of the gradient (tilt) direction A where the gradient strength (tilt strength) is the highest order and the gradient strength of the gradient (tilt) direction B where the gradient strength is the second order is the gradient bias feature amount Bb in the predetermined block.

Note that, as described above, in a case where the endoscopic image has a resolution of 1024×540, for example, if M=4 and N=4 are satisfied, the endoscopic image is divided into 125×87 blocks, for example.

In step S18, the feature amount generation unit 36 calculates the brightness Ib, and the chromaticity rb and gb in units of blocks of FIG. 5, and generates the four-dimensional feature amount together with the gradient bias feature amount.

More particularly, the feature amount generation unit 36 first operates the following Expressions (12) to (14) to calculate the lightness Isb and the chromaticity rsb and gsb in units of small blocks unit of FIG. 4 described above.

[Math. 12]

$$Isb(sx, sy) = \frac{1}{M \times N} \sum_{i=0}^{M} \sum_{j=0}^{N} I(sx \times M + i, sy \times N + j) \qquad (12)$$

[Math. 13]

$$rsb(sx, sy) = \frac{1}{M \times N} \sum_{i=0}^{M} \sum_{j=0}^{N} r(sx \times M + i, sy \times N + j) \qquad (13)$$

[Math. 14]

$$gsb(sx, sy) = \frac{1}{M \times N} \sum_{i=0}^{M} \sum_{j=0}^{N} g(sx \times M + i, sy \times N + j) \qquad (14)$$

Here, Isb is a feature amount of lightness in units of small blocks unit, and rsb and gsb are feature amounts of chromaticity in units of small blocks.

Next, the feature amount generation unit 36 operates the following Expressions (15) to (17) to calculate the lightness Ib and the chromaticity rb and gb in units of blocks unit of FIG. 5 described above.

[Math. 15]

$$Ib(bx, by) = \frac{1}{M \times N} \sum_{i=0}^{M} \sum_{j=0}^{N} Isb(bx + i, by + j) \qquad (15)$$

[Math. 16]

$$rb(bx, by) = \frac{1}{M \times N} \sum_{i=0}^{M} \sum_{j=0}^{N} rsb(bx + i, by + j) \qquad (16)$$

[Math. 17]

$$gb(bx, by) = \frac{1}{M \times N} \sum_{i=0}^{M} \sum_{j=0}^{N} gsb(bx + i, by + j) \qquad (17)$$

Here, (bx,by) represents the coordinate of the block. Ib is a feature amount of lightness in units of blocks, and rb and gb are feature amounts of chromaticity in units of blocks.

Then, the feature amount generation unit 36 generates a four-dimensional feature amount including the lightness Ib(bx,by), the chromaticity rb(bx,by), gb(bx,by), and the gradient bias feature amount Bb(x,y), and supplies the four-dimensional feature amount to the normalization adjustment unit 37.

Note that, as for the feature amount Bb(x,y), it is premised that two types of directions of the top two orders are adjacent, but the endoscopic image is smoothed by the processing of step S13 described above, and the gradient bias appears strongly, so that the upper gradient direction is the adjacent direction. Furthermore, the gradient direction of the second order may be adopted in a case where the gradient strength is larger than a predetermined value. In this case, in a case where the gradient strength of the gradient direction of the second order is smaller than a predetermined value, only the gradient strength of the gradient direction of the highest order may be adopted. Moreover, the sum of all of the gradient strengths in the gradient direction larger than a predetermined value may be adopted.

In step S19, the normalization adjustment unit 37 normalizes the four-dimensional feature amount so that the four-dimensional feature amount does not exceed a signal level such as 0 to 1, −1 to +1, for example, which is accepted by a classifier 51 described later, adjusts the degree of effect of the classifier 51 described later, or adjusts the degree of effect so that the degree is in accordance with development parameters, and supplies the adjusted four-dimensional feature amount to the image classification unit 38. More specifically, the normalization adjustment unit 37 normalizes and adjusts the four-dimensional feature amount by operating, for example, the following Expressions (18) to (21).

[Math. 18]

$$Ib'(bx,by)=(Ib(bx,by)-i\text{Offset})*i\text{Gain} \quad (18)$$

[Math. 19]

$$rb'(bx,by)=(rb(bx,by)-r\text{Offset})*r\text{Gain} \quad (19)$$

[Math. 20]

$$gb'(bx,by)=(gb(bx,by)-g\text{Offset})*g\text{Gain} \quad (20)$$

[Math. 21]

$$Bb'(bx,by)=(Bb(bx,by)-b\text{Offset})*b\text{Gain} \quad (21)$$

Here, Ib'(bx,by), rb'(bx,by), gb'(bx,by), Bb'(bx,by) are normalized and adjusted lightness, chromaticity, and the gradient bias feature amount, iOffset, rOffset, gOffset, bOffset are offset amounts of lightness, chromaticity, and gradient bias feature amount, and iGain, rGain, gGain, bGain are gain control coefficients.

In step S20, the image classification unit 38 controls the classifier 51 to classify the subject in the image using the normalized and adjusted four-dimensional feature amount, and supplies the classification result to the image processing unit 39.

Figure 7:
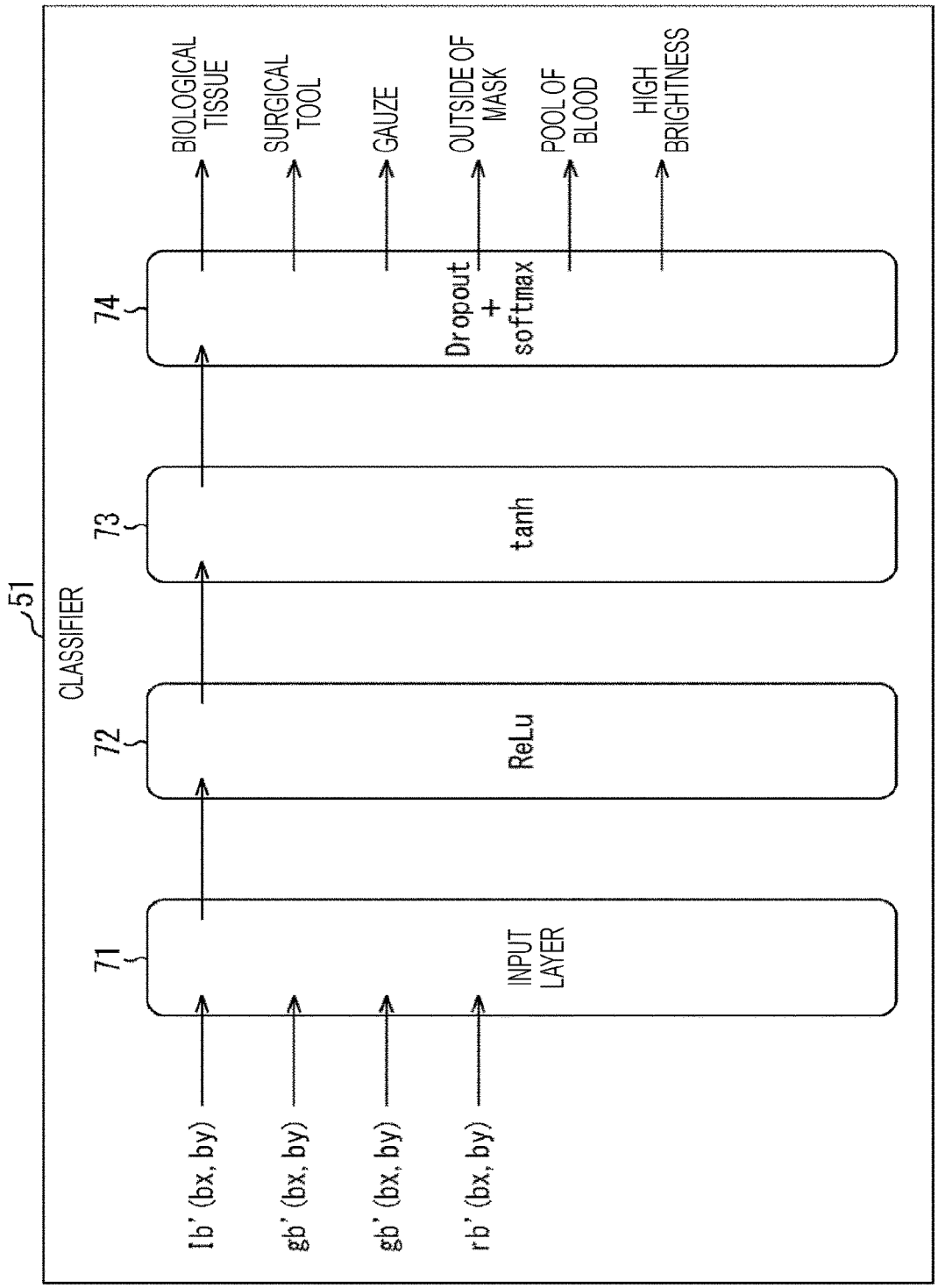
FIG. 7 is a diagram illustrating a configuration example of a classifier using a neural network.

The classifier 51 may have a configuration using, for example, a neural network. FIG. 7 shows a configuration example of the classifier 51 configured by using a neural network. The classifier 51 of FIG. 7 includes an input layer 71, ReLu 72, tanh 73, and Dropout+softmax 74.

The input layer 71 accepts the four-dimensional feature amount and supplies the four-dimensional feature amount to the ramp function (ReLu) 72.

Figure 8:
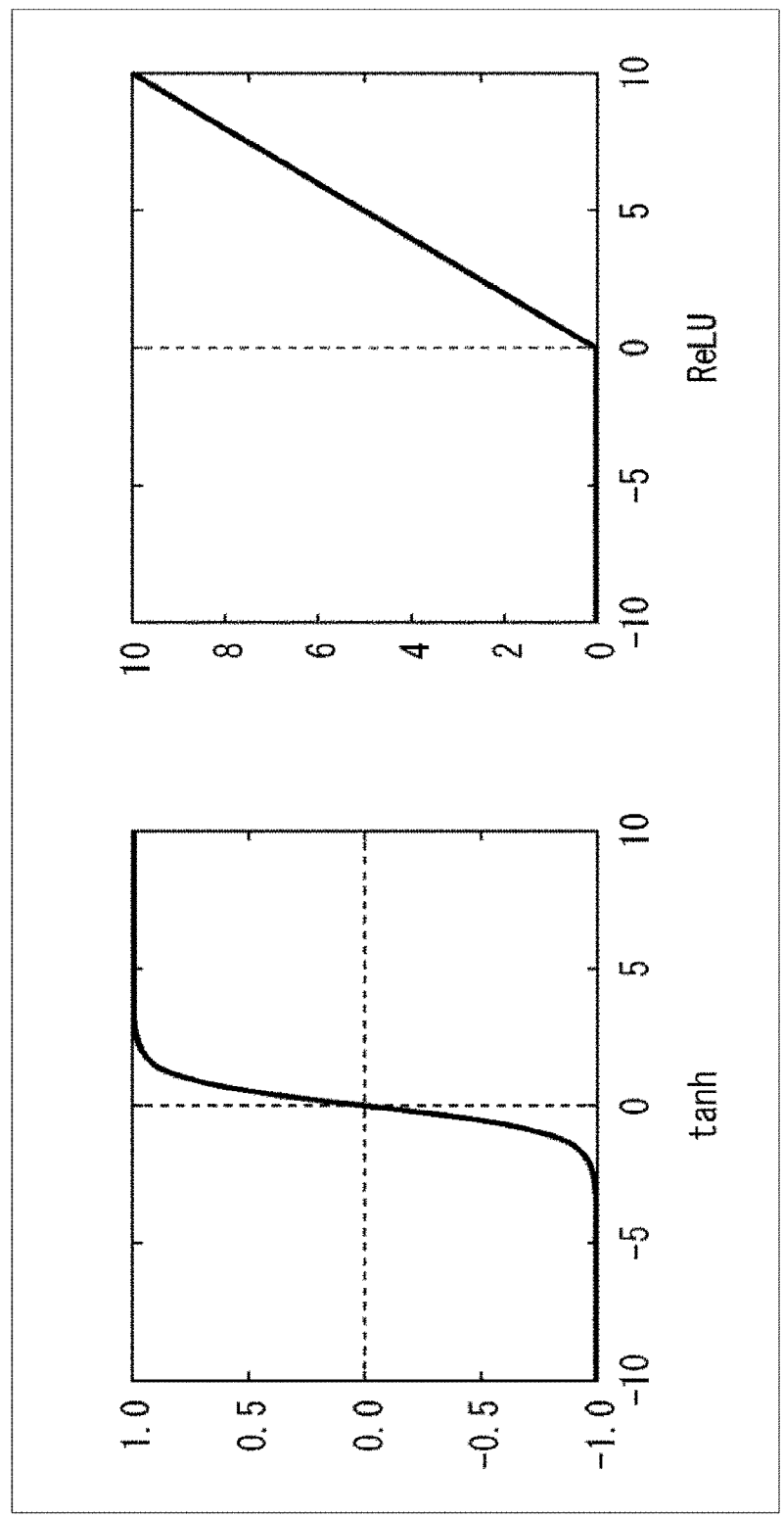
FIG. 8 is a diagram illustrating characteristics of Tanh and ReLu.

The ramp function (ReLu) 72 is, for example, a function as shown in the right part of FIG. 8, performs processing using this function on the four-dimensional feature amount, and supplies the processed four-dimensional feature amount to the tanh 73.

The tanh 73 is, for example, a function as shown in the left part of FIG. 8, and performs processing by the function as shown in the left part of FIG. 8 on the four-dimensional feature amount processed by the ramp function 72, and supplies the processed four-dimensional feature amount to Dropout+softmax 74.

The Dropout+softmax 74 includes Dropout and softmax. Among these, the Dropout is a function for preventing excessive learning of the network at the time of learning, and for example, performing processing simply making output of elements half. Furthermore, the softmax is mainly used to normalize an output value of a neural network having a classification function, and is represented by the following Expression (22), for example.

[Math. 22]

$$\phi(u_k) = \frac{e^{u_k}}{\sum_{i=0}^{K} e^{u_i}} \quad (22)$$

With these configurations, the classifier 51 classifies, for example, a biological tissue, a surgical tool, gauze, an outside of a mask, a pool of blood, and a high brightness portion on the basis of the four-dimensional feature amount. More particularly, the classifier 51 classifies a region being a surgical tool, gauze, an outside of a mask, a pool of blood, or a high brightness portion by the four-dimensional feature amount, and classifies the region not classified as those, as a biological.

More specifically, for example, in a case of classifying a surgical tool, gauze, an outside of a mask, a pool of blood, a high brightness portion, and a biological tissue, the classifier 51 classifies the subject in units of frames F11. For example, for a surgical tool and gauze, if the block of FIG. 5 classified as an outside of a mask is not included, and the number of blocks determined as surgical tools is larger than the number of blocks determined as gauze, the classifier 51 regards it as a surgical tool, and if it is reverse, regards it as gauze.

Furthermore, for example, if the number of blocks in FIG. 5 classified as an outside of a mask, a pool of blood, and high brightness portion in each frame F11 is equal to or more than a predetermined ratio, the classifier 51 regards it as an outside of a mask, a pool of blood, or a high brightness portion. Then, the classifier 51 regards the frame F11 that is not regarded as any of a surgical tool, gauze, an outside of a mask, a pool of blood, and a high brightness portion as a biological tissue.

With such a classification, by detecting a surgical tool, gauze, an outside of a mask, a pool of blood, and a high brightness portion which are detectable even if the classification accuracy of the classifier 51 is not so high, and recognizing other portions as biological tissue, it is possible to classify the biological tissue with high accuracy while reducing the processing load related to similarity.

Furthermore, regarding the classification result of the classifier 51, a score for each classification target such as a surgical tool, gauze, an outside of a mask, a pool of blood, a high brightness portion, or a biological tissue may be calculated for each frame F11 so that the classification result is determined in accordance with the score. In this case, the classification target with the highest score may be used as the classification result, or the classification result up to the second order may be presented to be selectable. Moreover, when presenting the classification results up to the second order, for the classification target of the score of the second order, only in the case where the score is a predetermined score or more, up to the second order may be presented to be selectable. Note that, in the present disclosure, an example of classifying gauze, an outside of a mask, a pool of blood, a high brightness portion, and biological tissue has been described. However, other subjects may be classified. However, when biological tissue is classified, it is similar that the range is not classified as other subjects.

In step S21, the image processing unit 39 performs image processing on the imaged endoscopic image on the basis of the classification result, and supplies the processing result to the AE control unit 42, the AF control unit 43, and the blur correction unit 44.

Figure 9:
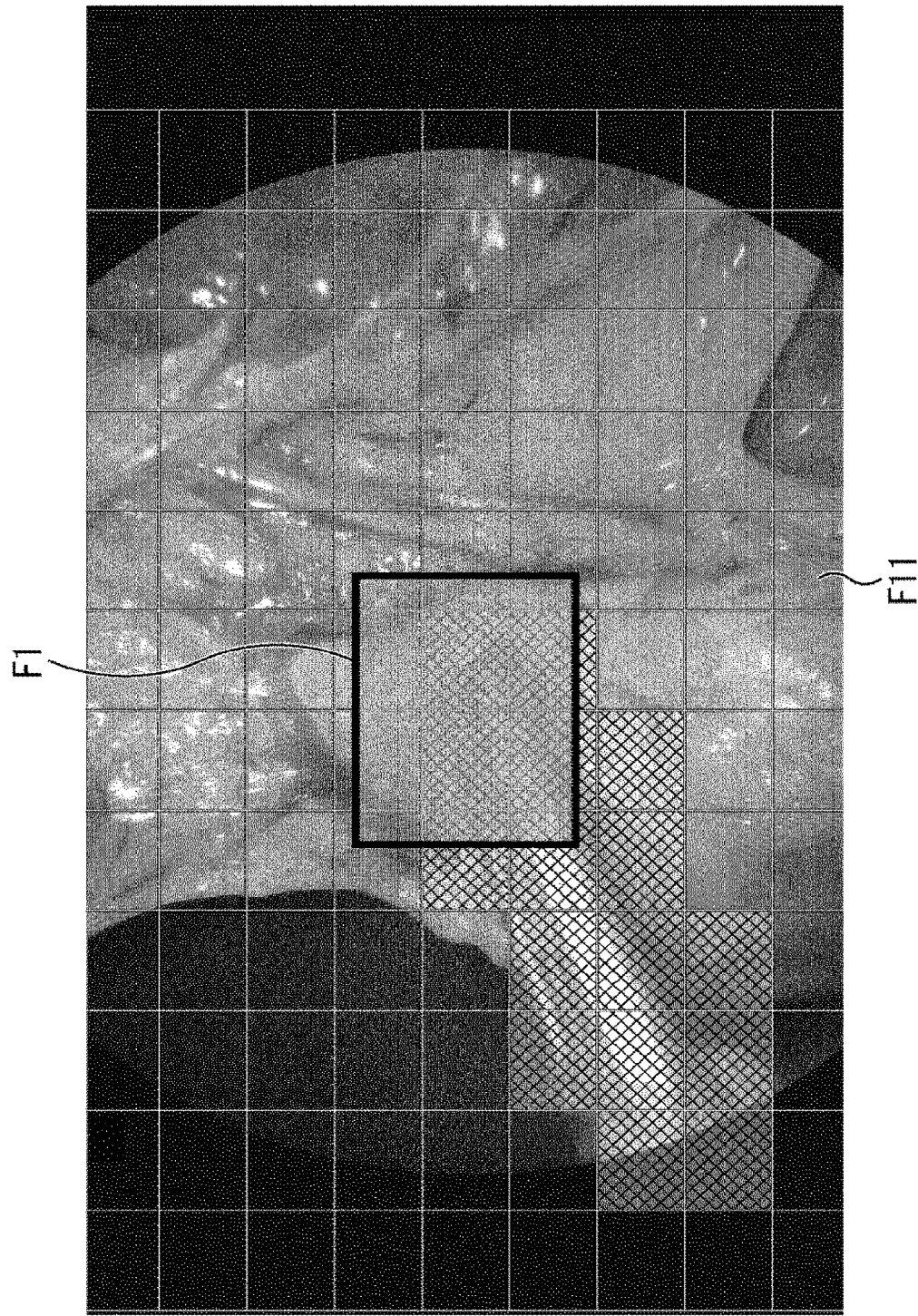
FIG. 9 is a diagram illustrating a display example of an endoscopic image displayed on an image display unit.

More specifically, for example, as shown in FIG. 9, in a case where a range in which a forceps K exists is detected as a surgical tool, the image processing unit 38 hatches the corresponding range of the endoscopic image with colors, patters, or the like indicating that the range is a classified surgical tool. Besides this, AE, AF, blur correction, and the like may be affected, and the region other than biological tissue is hatched with colors, patterns or the like in accordance with the classification result.

For example, there are other possibilities that may affect AE, AF, shake correction, and the like, such as gauze, out of mask, blood pool, or high luminance part, and the region other than biological tissue is hatched with colors, patterns or the like in accordance with the classification result. Note that, the range of biological tissue is regarded as an outside of the range recognized as gauze, an outside of a mask, a pool of blood, or a high brightness portion.

Note that, in FIG. 9, the frame F11 provided in a lattice shape is a block for controlling the AE and blur correction by the AE control unit 42 and the blur correction unit 44, and a single frame F1 formed by a thick line indicates a range in which AF is controlled by the AF control unit 43. Both the frames F1 and F11 are set to sizes suitable for controlling each of the AE control, the AF control, and the blur correction, and are larger than the blocks in FIG. 5 described above. In other words, the block in FIG. 5 is the minimum processing unit in the processing of AE and AF using the frames F1 and F11.

Figure 10:
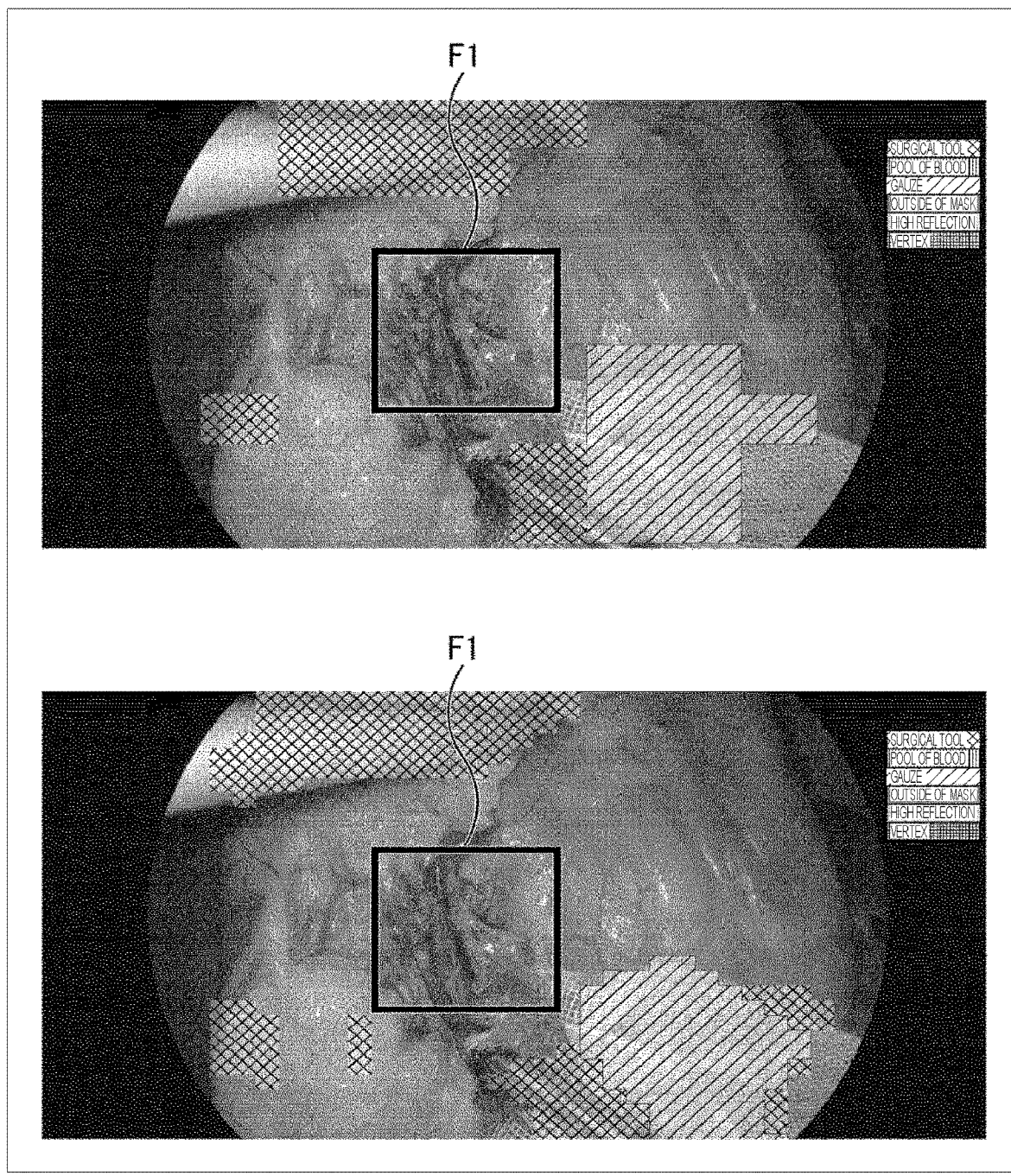
FIG. 10 is a diagram illustrating a display example of an endoscopic image displayed on an image display unit.

For example, in a case where the size of the frame F11 is, for example, a size for dividing into 12×5 with respect to the endoscopic image, the hatching range is as shown in the upper part of FIG. 10. However, in the case of, for example, a size for dividing into 40×30 with respect to the endoscopic image, the hatching range is as shown in the lower part of FIG. 10. In other words, in a case where the size of the frame F11 is smaller than the size shown in the lower part of FIG. 10, it is possible to set the range with higher resolution than the case of the large size as shown in the upper part of FIG. 10.

Note that, in the above description, an example in which the classifier 51 is configured by a neural network has been described. However, other configurations may be adopted as long as a device functions as the classifier 51, for example, a device using machine learning, typified by Boosting or the like.

In step S22, the AE control unit 42 controls AE using brightness information in units of frames F11 within the range regarded as biological tissue. In other words, such processing prevents AE control using even a pixel that is likely to color out due to light reflected by a metal surgical tool or the like, and therefore, appropriate AE control can be realized.

In other words, as shown in the upper part or the lower part of FIG. 10, the range in which a surgical tool is imaged and the range in which gauze is imaged are hatched with distinctive colors, patterns, or the like, and brightness information in the frame F11 in the other range is utilized to realize AE. As a result, AE is realized in a state where only the brightness information of the range in which the biological tissue is imaged is used, so that appropriate AE can be realized. Note that, since the required brightness may differ depending on the type of operation, clinical department, or the like, AE is controlled so that the brightness is suitable for each case.

In step S23, the AF control unit 43 realizes the AF utilizing the image in the range regarded as biological tissue. More particularly, the AF control unit 43 moves the frame F1 of a predetermined size in the image until the frame F1 reaches a position including only biological tissue in the vicinity of the center of the endoscopic image, and searches a region of interest. At this time, in a case where the region of interest cannot be searched, the size of the frame F1 is made smaller, and the region of interest is searched repeatedly by the frame F1 until the region of interest can be searched.

Then, when the region of interest can be searched, the AF control unit 43 realizes the AF control by using the image in the region of interest. More specifically, for example, AF control is realized by searching a focused state by edge detection.

In other words, as shown in the upper part of FIG. 10, the AF control unit 43 moves the frame F1 up to a position not including the hatched region.

When the region of interest can be specified by the frame F1, the AF control unit 43 controls the optical block 61 so that the edge is sufficiently detected to realize the AF control. By detecting the edge of the region of interest specified by the frame F1 including only biological tissue in this manner to realize AF, appropriate AF control can be realized.

In step S24, the blur correction unit 44 corrects blur using motion information within a range regarded as biological tissue.

Figure 11:
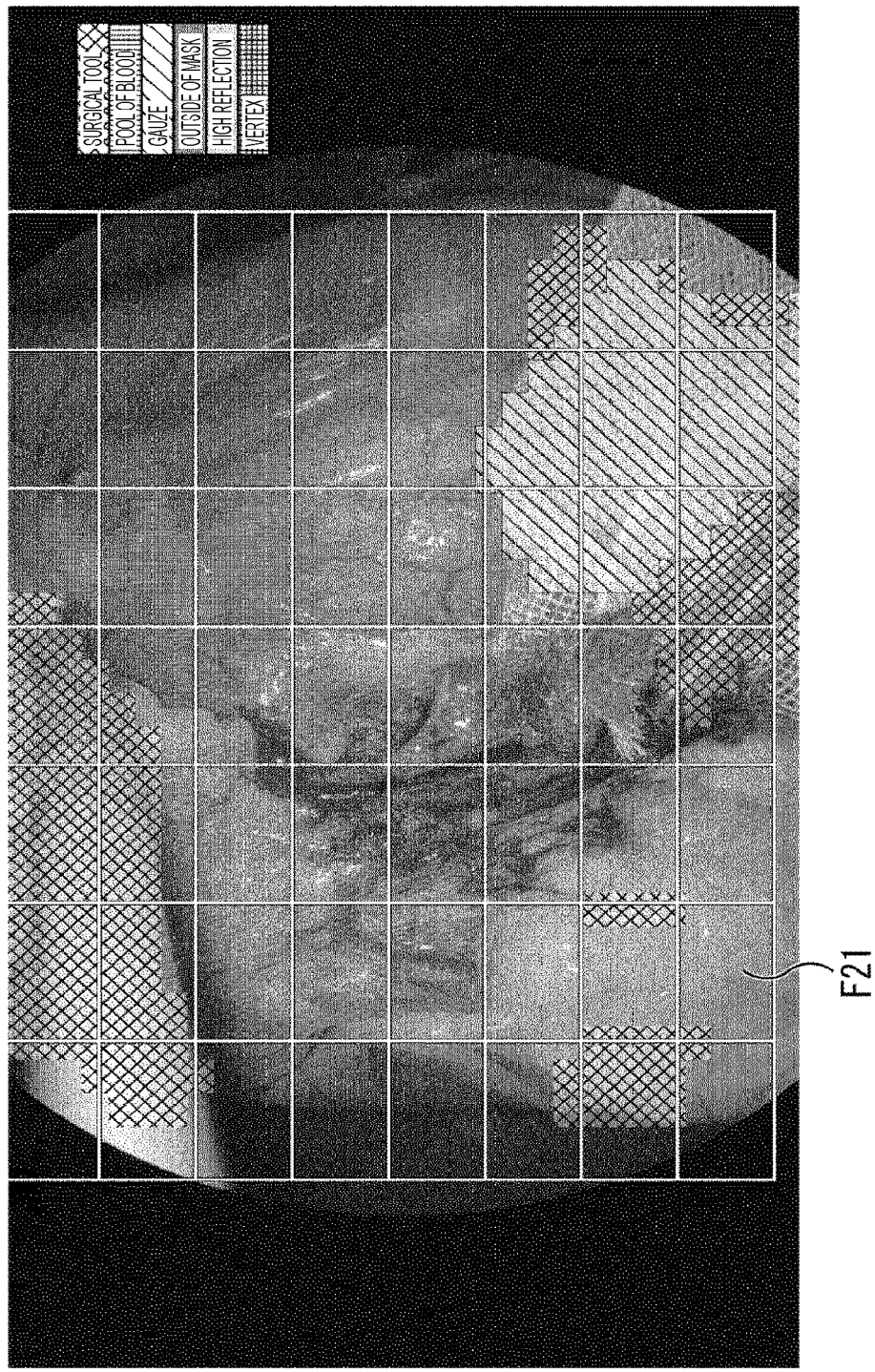
FIG. 11 is a diagram illustrating a display example of an endoscopic image displayed on an image display unit.
Figure 12:
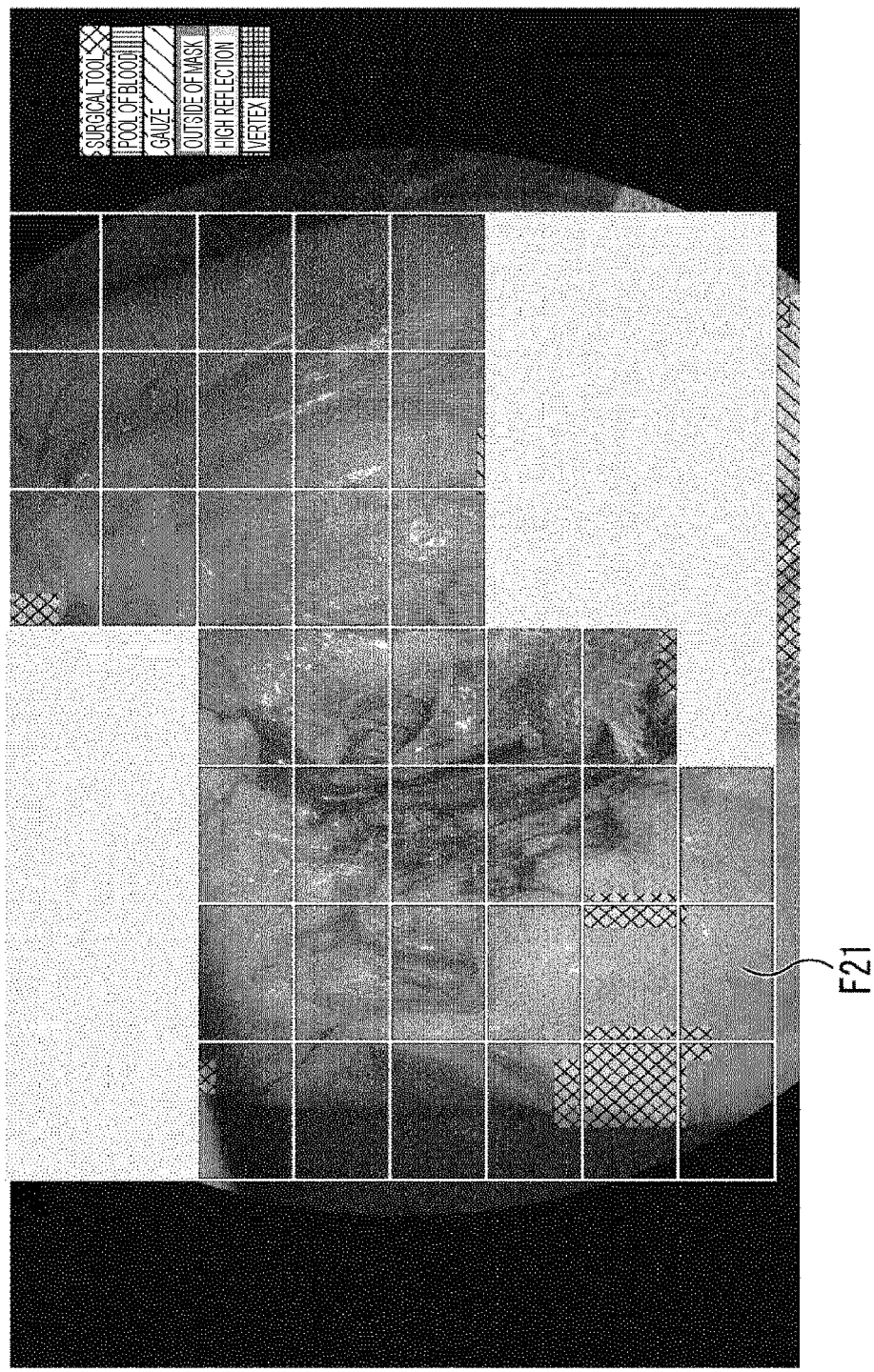
FIG. 12 is a diagram illustrating a display example of an endoscopic image displayed on an image display unit.

In other words, as shown in FIG. 11, the blur correction unit 44 hatches white as shown in FIG. 12 when searching is performed for the range in which a surgical tool has been imaged and the range in which gauze is imaged. Then, the blur correction unit 44 utilizes motion realizes motion compensation using motion information in a frame F21 of a range other than the hatched range. As a result, blur is corrected in a state where only the motion information of the range in which the biological tissue is imaged is used, so that appropriate blur correction can be realized.

In step S25, the image processing unit 39 supplies the processed image to the display control unit 40 so as to cause the display control unit 40 to control the display on the image display unit 13. With respect to the image displayed here, images that have been subjected to AE, AF, and blur correction are displayed. In other words, by the above processing, it is possible to present an endoscopic image that has been subjected to appropriate AE, AF, and blur correction, and present a biological tissue being a viewing target in an easy-to-view manner for a doctor who is an operator.

In step S26, the image classification unit 38 determines whether or not re-learning has been instructed by operating the operation unit 41. In a case where re-learning is instructed, processing proceeds to step S27.

In step S27, the image classification unit 38 performs re-learning processing and causes the classifier 51 to perform re-learning. Note that the relearning processing will be described later with reference to the flowchart of FIG. 14.

Note that, in a case where re-learning has not been instructed in step S26, the processing of step S27 is skipped.

In step S28, the image processing device 11 determines whether or not termination has been instructed. In a case where termination is not instructed, the processing returns to step S11 and the subsequent processing is repeated. Then, in a case where termination is instructed in step S28, the processing is terminated.

Figure 13:
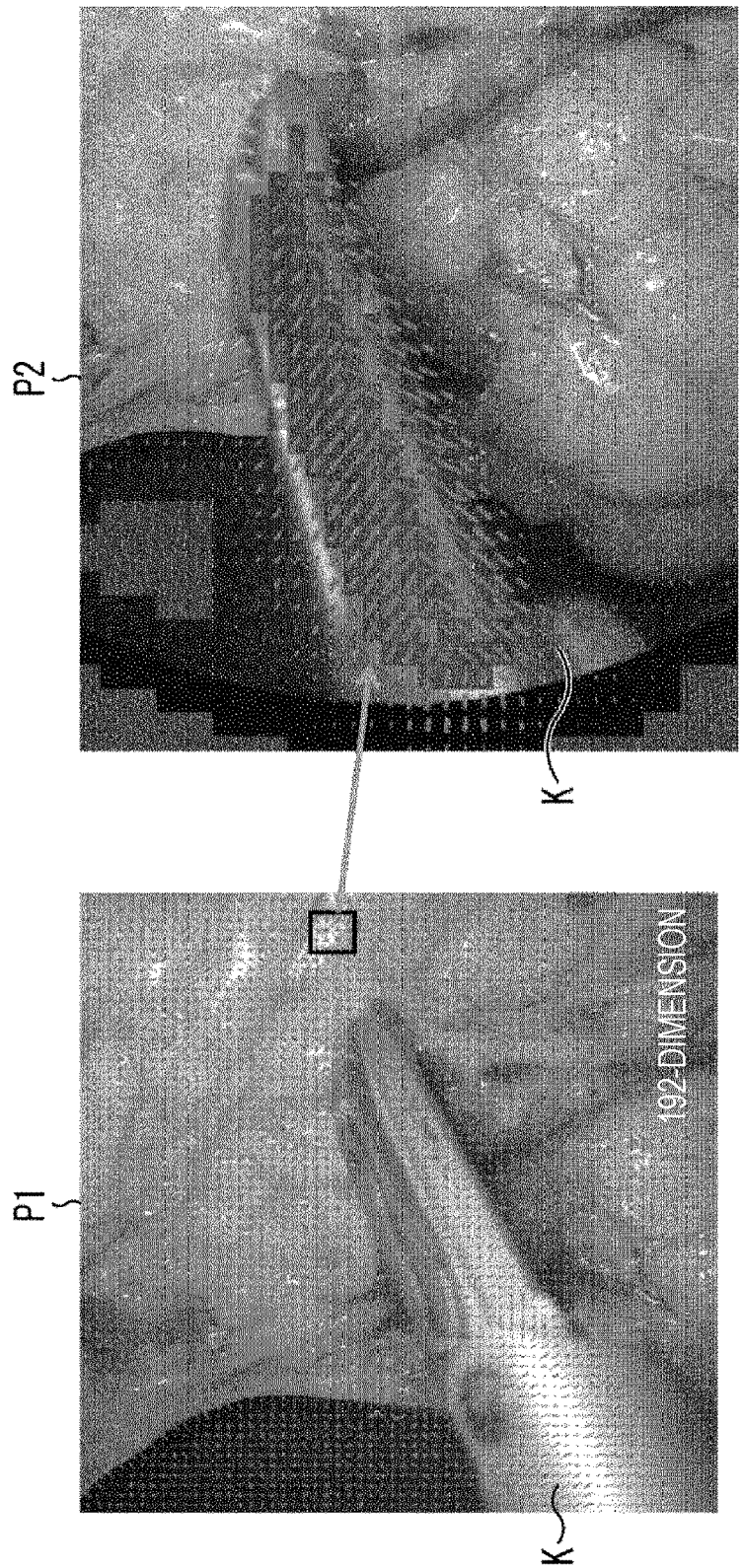
FIG. 13 is a diagram illustrating image processing by an image processing device of the present disclosure.

Here, the above processing is summarized with reference to FIG. 13.

In other words, in a case of an image P1 of FIG. 13 in which the forceps as the surgical tools are displayed in front of the biological tissue, in a step S16, general HOG is obtained as a set of histograms in the image tilt direction in units of small blocks.

Therefore, as shown by a rectangular frame of the image P1 in FIG. 13, for example, if each block has histograms in 12 directions gradient directions for the range of 4 blocks×4 blocks, information thereof is 4×4×12=192 dimensional information.

However, in the image processing device 11 of the present disclosure, the original endoscopic image is multiplied by LPF and smoothed and then HOG is obtained, so that a strong gradient is generated in a wide range. Moreover, in the smoothed image, gradient strength (frequency) histograms for gradient directions of each block in the range of 4 blocks×4 blocks are summed, and the one-dimensional information including only the sum of the gradient strengths up to the second order is used as the gradient bias feature amount, so that representation as the gradient bias as shown in an image P2 of FIG. 13 can be performed. For this reason, since it becomes possible to perform classification with feature amount with a small number of dimensions, the operation amount related to classification can be reduced. Note that, in the images P1 and P2 of FIG. 13, the gradient direction and the gradient strength of each block are expressed on the image in terms of the thickness and the length of the rod-like gauge and the inclined direction. Furthermore, in the image P2, hatching indicating that a surgical tool is detected in the portion of the forceps K is applied. Moreover, the rod-like gauge on the image P2 indicated by the arrow from the rectangular frame on the image P1 is an example in which the 192-dimensional gradient bias feature amount in the frame is represented in one dimension.

Moreover, with respect to the range of the biological tissue, a tool, gauze, and the like that are relatively easy to classify are classified, and with respect to biological tissue that is difficult to classify is regarded as the outside of the range that is easy to classify, and thereby, in an endoscopic image imaged by the endoscope device 12, the range being biological tissue can be classified with low delay and presented while the operation amount is reduced.

Re-Learning Processing

Figure 14:
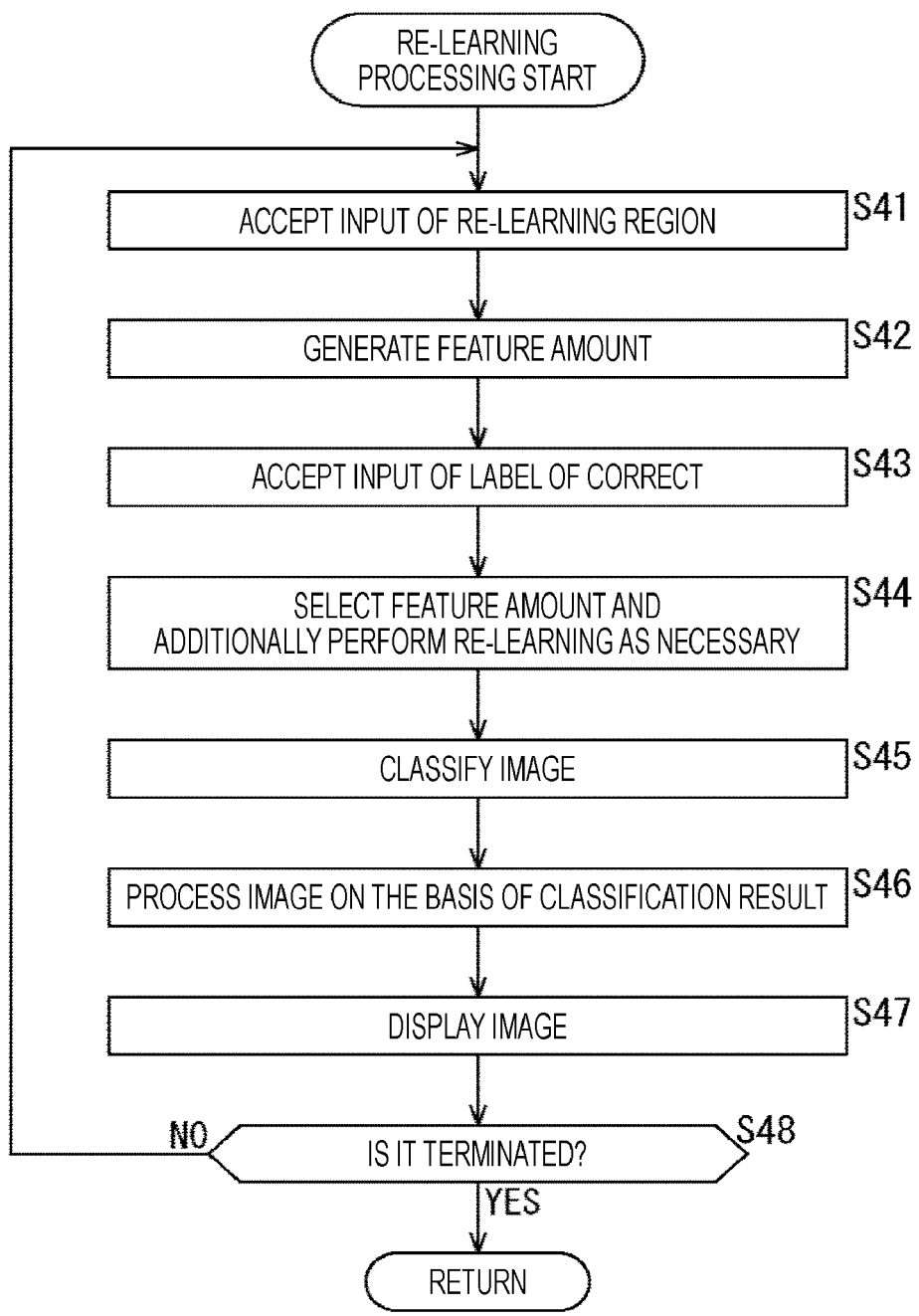
FIG. 14 is a flowchart illustrating re-learning processing.

Next, the re-learning processing will be described with reference to the flowchart of FIG. 14.

In step S41, the operation unit 41 is operated and the image classification unit 38 accepts an input of a re-learning region on the image display unit 13.

In step S42, the image classification unit 38 reads a four-dimensional feature amount in a block belonging to the re-learning region.

In step S43, the image classification unit 38 accepts an input of a correct label.

In step S44, the image classification unit 38 controls the classifier 51 to classify a four-dimensional feature amount, add it as necessary, and learn so as to obtain a correct label.

In step S45, the image classification unit 38 controls the classifier 51 that has finished re-learning, to classify the image by using the four-dimensional feature amount accepted as the re-learning region, and supply the classification result to the image processing unit 39.

In step S46, the image processing unit 39 processes the image on the basis of the classification result.

In step S47, the image processing unit 39 supplies the image processing result to the display control unit 40, to control the display on the image display unit 13.

In step S48, the image classification unit 38 determines whether or not the re-learning process is terminated. For example, in the case where there is an error in classification and re-learning is necessary again, when the operation unit 41 is operated and an instruction regarding the necessity is given, the processing returns to step S41 and the subsequent processing is repeated. Then, if termination is instructed in step S48, the processing ends.

Figure 15:
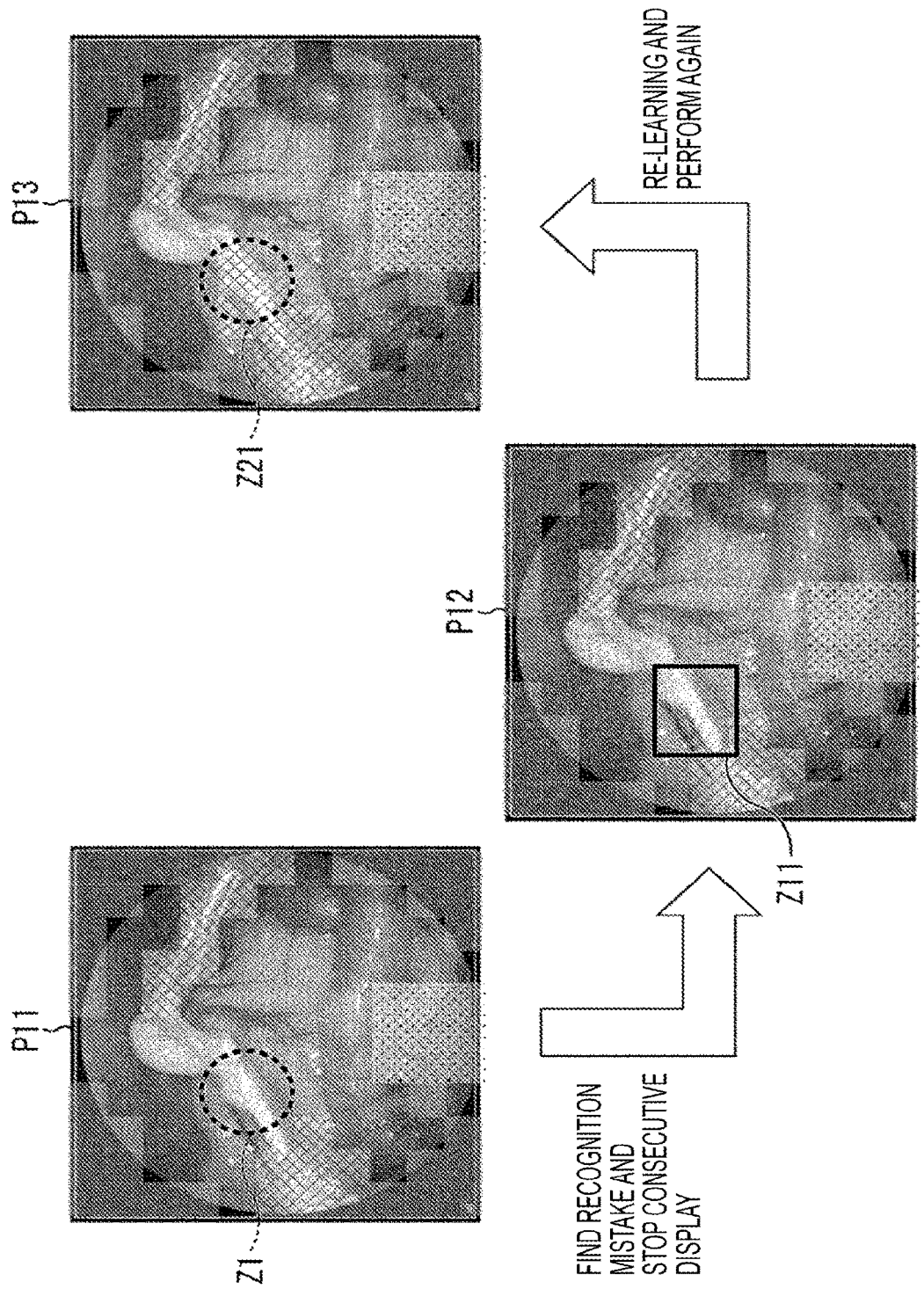
FIG. 15 is a diagram illustrating re-learning processing.

In other words, as shown in the image P11 in FIG. 15, in a case where a range Z1 in which the forceps K exists is not hatched and is not classified as a surgical tool, a doctor who is an operator, for example, as shown by an image P12, regards this case as a recognition mistake due to classification, and a range Z11 is specified as the re-learning region. Then, after the usual display is stopped, the four-dimensional feature amount of the block in the corresponding range is selected and furthermore, re-learning is performed by processing such as adding as necessary, as shown in a range Z21 of an image P13, the range can be classified as a surgical tool and hatched.

Note that, in the above description, AE, AF, and blur correction of the endoscopic image have been described. However, as long as the image is imaged under similar conditions as the endoscopic image, the image is not limited to the endoscopic image. Similar effects can be obtained even with other images, and for example, similar effects can be obtained even with a microscopic image or the like.

As described above, according to the present disclosure, even in the case of a so-called out-of-focus image or out-of-exposure state in which a viewing target in an endoscopic image is out of focus, a position of an object such as a surgical tool or gauze that may decrease accuracy of imaging control such as AE, AF, and blur correction can be specified.

As a result, a range other than the range where the position of the object is specified can be classified as biological tissue, and appropriate AE, AF and blur correction targeting biological tissue can be realized. As a result, an endoscopic image easy to view for the operator can be presented with low delay.

Furthermore, in a case where failure occurs in classification, re-learning based on correct labels can be performed by causing re-learning processing to be performed each time, so the difficulty of viewing can be quickly eliminated, and an endoscopic image easy to view can be presented.

3. Application Example

Example of Executing by Software

Incidentally, the series of processing described above can be also executed by hardware. However, the series of processing can also be executed by software. In a case of executing a series of processing by software, a program included in the software is installed from a recording medium to a computer incorporated in dedicated hardware, for example, a general personal computer that can execute various functions by installing various programs, or the like.

Figure 16:
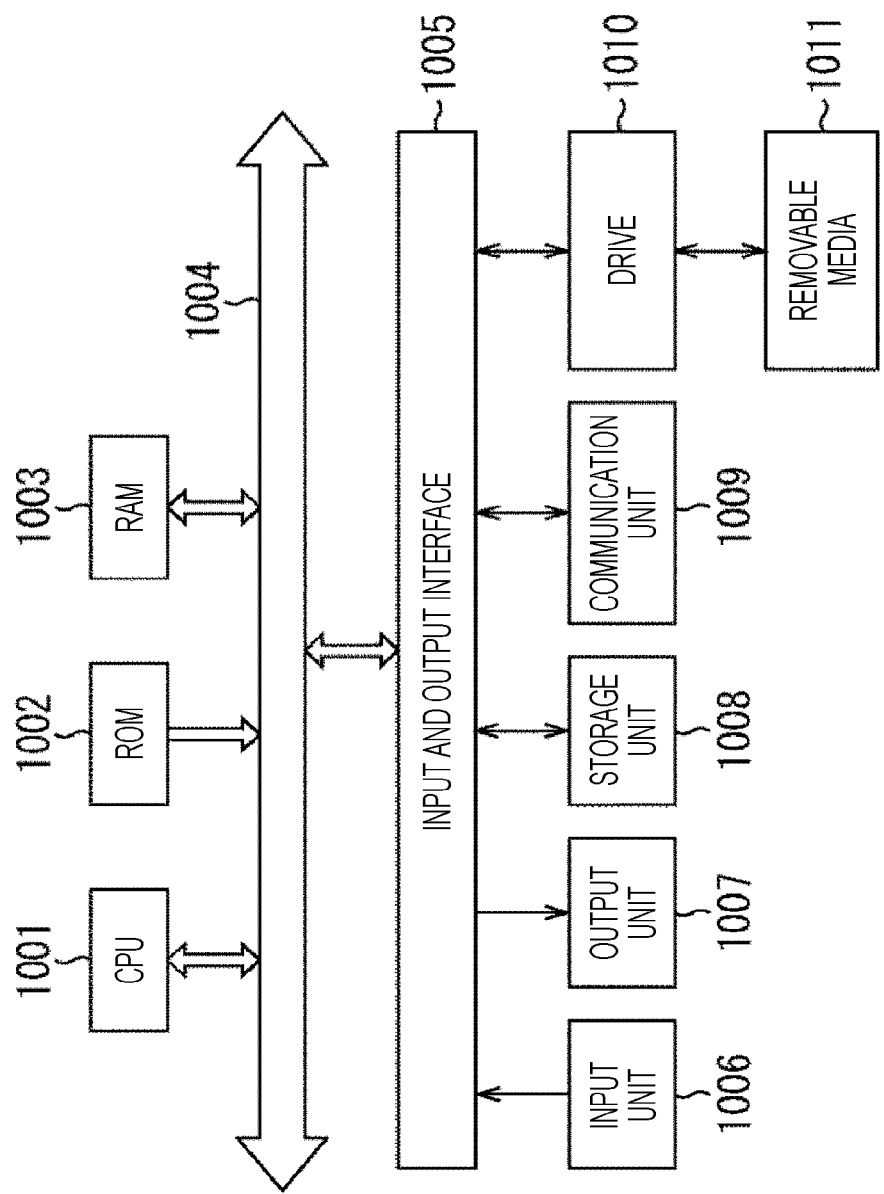
FIG. 16 is a diagram showing a configuration example of a general-purpose personal computer.

FIG. 16 shows a configuration example of a general-purpose personal computer. This personal computer has a built-in central processing unit (CPU) 1001. An input and output interface 1005 is connected to the CPU 1001 via a bus 1004. A read only memory (ROM) 1002 and a random access memory (RAM) 1003 are connected to the bus 1004.

The input and output interface 1005 is connected with an input unit 1006 including an input device such as a keyboard, or a mouse for inputting operation commands by the user, an output unit 1007 that outputs an image of a processing operation screen or a processing result to a display device, a storage unit 1008 including a hard disk drive or the like for storing programs and various data, and a communication unit 1009 including a local area network (LAN) adapter or the like and performing communication processing via a network typified by the Internet. Furthermore, the input and output interface 1005 is connected with a drive 1010 that reads and writes data with respect to a removable medium 1011 such as a magnetic disc (including a flexible disc), an optical disc (including compact disc-read only memory (CD-ROM) and a digital versatile disc (DVD)), or a semiconductor memory.

The CPU 1001 is read out from a program stored in the ROM 1002 or the removable medium 1011 such as a magnetic disc, an optical disc, a magneto-optical disc, or a semiconductor memory, is installed in the storage unit 1008, and executes various processing in accordance with a program loaded into the RAM 1003 from the storage unit 1008. Furthermore, the RAM 1003 appropriately stores also data or the like necessary for the CPU 1001 to execute various processing.

In the computer configured as described above, for example, the CPU 1001 loads the program stored in the storage unit 1008 into the RAM 1003 via the input and output interface 1005 and the bus 1004, and executes the program, so that the above-described series of processing is performed.

The program executed by the computer (CPU 1001) can be provided by being recorded on the removable medium 1011 as a package medium or the like, for example. Furthermore, the program can be provided via a wired or wireless transmission medium such as a local area network, the Internet, or digital satellite broadcasting.

In a computer, a program can be installed in the storage unit 1008 via the input and output interface 1005 by mounting the removable medium 1011 to the drive 1010. Furthermore, the program can be received by the communication unit 1009 via a wired or wireless transmission medium and installed in the storage unit 1008. In addition, the program can be installed in the ROM 1002 or the storage unit 1008 in advance.

Note that the program executed by the computer may be a program of processing in chronological order according to the order described in the present specification or may be a program of processing in parallel or at necessary timing such as when a call is made.

Furthermore, in this specification, a system means a set of a plurality of constituent elements (devices, modules (parts), or the like), and it does not matter whether or not all constituent elements are in the same casing. Therefore, a plurality of devices that are housed in separate housings and are connected via a network, and one device in which a plurality of modules are housed in one housing are both systems.

Note that the embodiments of the present disclosure are not limited to the above-described embodiments, and various modifications are possible without departing from the gist of the present disclosure.

For example, in the present disclosure, it is possible to adopt a configuration of cloud computing in which one function is shared by a plurality of devices via a network, and is collaboratively processed.

Furthermore, each step described in the above-described flowchart can be executed by one device or shared by a plurality of devices.

Moreover, in a case where a plurality of processes are included in one step, a plurality of processes included in the one step can be executed by one device or shared by a plurality of devices.

Note that, the present disclosure can adopt the following configuration.

<1> An image processing device including:
a smoothing unit that smooths a biological image generated by imaging an inside of a biological body including a biological tissue by a medical imaging device; and
a classification unit that classifies each subject included in each region in the biological image on the basis of a smoothed image obtained by smoothing the biological image by the smoothing unit.

<2> The image processing device described in <1> in which
the classification unit classifies the each subject included in the each region into the biological tissue or one other than the biological tissue on the basis of the smoothed image.

<3> The image processing device described in <2> in which
the classification unit classifies the each subject included in the each region on the basis of lightness, chromaticity, and brightness of the smoothed image.

<4> The image processing device described in <3> further including:
a conversion unit that converts a pixel value of each pixel of the smoothed image into lightness, chromaticity, and brightness; and
a brightness gradient calculation unit that obtains a gradient direction and a gradient strength of the brightness of each pixel in the smoothed image,
in which the classification unit classifies a subject in the biological image on the basis of the lightness, the chromaticity, and the gradient direction and the gradient strength, in units of blocks of a predetermined size in the biological image.

<5> The image processing device described in <4> in which
the block of a predetermined size includes a plurality of small blocks having a size smaller than the predetermined size, and
the image processing device further includes a gradient bias calculation unit that obtains a moving addition of a histogram of a gradient strength in units of small blocks to obtain a histogram being the moving addition as a gradient bias feature amount in units of small blocks.

<6> The image processing device described in <5> in which
the gradient bias calculation unit obtains a moving addition of a histogram of a gradient strength of a plurality of the small blocks in units of the blocks to calculate a gradient strength of higher order of a histogram being the moving addition as a gradient bias feature amount in units of the blocks of the predetermined size, and
the classification unit classifies a subject in the biological image on the basis of the lightness, the chromaticity, and the gradient bias feature amount in units of blocks.

<7> The image processing device described in <6> in which
the gradient bias calculation unit calculates a sum of gradient strength up to a predetermined higher order of the histogram being the moving addition as the gradient bias feature amount in units of the blocks of the predetermined size.

<8> The image processing device described in <2> in which
the classification unit classifies one other than the biological tissue into any of a surgical tool, gauze, an outside of a mask, a pool of blood, or a high brightness portion in the biological image.

<9> The image processing device described in <8> in which
the classification unit classifies the each subject included in the each region in the biological image into any of a surgical tool, gauze, an outside of a mask, a pool of blood, or a high brightness portion other than a biological tissue, and classifies a subject in a region not classified as any type as a biological tissue.

<10> The image processing device described in <1> in which
the classification unit includes a classifier using a neural network.

<11> The image processing device described in <1> in which
the classification unit includes a classifier using machine learning using boosting.

<12> The image processing device described in <2> further including
an exposure adjustment unit that adjusts exposure in the medical imaging device on the basis of information regarding brightness of the region classified as the biological tissue in the biological image.

<13> The image processing device described in <2> further including
a focus adjustment unit that adjusts focus in the medical imaging device on the basis of only information of the region classified as the biological tissue in the biological image.

<14> The image processing device described in <2> further including
a blur correction unit that corrects blur in the biological image on the basis of information regarding moving of the region classified as the biological tissue in the biological image.

<15> The image processing device described in <1> further including:
an image processing unit that processes an image so as to hatch a position on the biological image corresponding to a type of a classified subject on the basis of a classification result of the classification unit; and
a display control unit that controls display of the biological image processed by the image processing unit.

<16> The image processing device described in <15> further including
an operation unit that specifies a re-learning range requiring re-learning and specifies a correct label indicating a correct subject on the displayed biological image,
in which the classification unit performs re-learning so as to classify a subject corresponding to the correct label in the re-learning range.

<17> The image processing device described in <1> in which
the biological image is an endoscopic image imaged by an endoscope device.

<18> An image processing method including steps of:
smoothing an image;
smoothing a biological image generated by imaging an inside of a biological body including a biological tissue by a medical imaging device; and
classifying each subject included in each region in the biological image on the basis of a smoothed image obtained by smoothing the biological image.

<19> A medical imaging system including:
an image processing device including
a smoothing unit that smooths a biological image generated by imaging an inside of a biological body including a biological tissue by a medical imaging device, and
a classification unit that classifies each subject included in each region in the biological image on the basis of a smoothed image obtained by smoothing the biological image by the smoothing unit; and
a medical imaging device including
an imaging unit that images the image.

REFERENCE SIGNS LIST

11 Image processing device
12 Endoscope device
13 Image display unit
14 Patient
31 Image reduction unit
32 Image smoothing unit
33 Luminance chromaticity conversion unit
34 Brightness gradient calculation unit
35 Gradient bias calculation unit
36 Feature amount generation unit
37 Normalization adjustment unit
38 Image classification unit
39 Image processing unit
40 Display control unit
41 Operation unit
42 AE control unit
43 AF control unit
44 Blur correction unit
51 Classifier
71 Input layer
72 ReLu
73 tanh
74 Dropout+softmax

The invention claimed is:

1. An image processing device comprising:
processing circuitry configured to
smooth a biological image generated by imaging an inside of a biological body including a biological tissue by a medical imaging device;
convert a pixel value of each pixel of the smoothed biological image into lightness, chromaticity, and brightness;
calculate, based on the brightness, a gradient direction and a gradient strength of the brightness of the each pixel in the smoothed image; and
classify, based on the smoothed image, each subject included in each region in the biological image into the biological tissue or one other than the biological tissue, based on the lightness, the chromaticity, the gradient direction and the gradient strength, in units of blocks of a predetermined size in the biological image.

2. The image processing device according to claim 1, wherein
the block of the predetermined size includes a plurality of small blocks having a size smaller than the predetermined size, and
the processing circuitry is further configured to obtain a moving addition of a histogram of a gradient strength in units of the small blocks to obtain a histogram being the moving addition as a gradient bias feature amount in units of the small blocks.

3. The image processing device according to claim 2, wherein
the processing circuitry is further configured to:
obtain a moving addition of a histogram of a gradient strength of the plurality of the small blocks in units of the blocks to calculate a gradient strength of higher order of a histogram being the moving addition as a gradient bias feature amount in units of the blocks of the predetermined size; and
classify a subject in the biological image based on the lightness, the chromaticity, and the gradient bias feature amount in units of blocks.

4. The image processing device according to claim 3, wherein
the processing circuitry is configured to calculate a sum of gradient strength up to a predetermined higher order of the histogram being the moving addition as the gradient bias feature amount in units of the blocks of the predetermined size.

5. The image processing device according to claim 1, wherein
the processing circuitry is configured to classify one other than the biological tissue into any of a surgical tool, gauze, an outside of a mask, a pool of blood, or a high brightness portion in the biological image, the high brightness portion having brightness higher than a threshold.

6. The image processing device according to claim 5, wherein
the processing circuitry is configured to:
classify the each subject included in the each region in the biological image into any types of the surgical tool, the gauze, the outside of the mask, the pool of blood, or the high brightness portion other than the biological tissue, and
classify a subject in a region not classified as any of the types as the biological tissue.

7. The image processing device according to claim 1, wherein
the processing circuitry is configured to classify the each subject using a neural network.

8. The image processing device according to claim 1, wherein
the processing circuitry is configured to classify the each subject using machine learning using boosting.

9. The image processing device according to claim 1, wherein the processing circuitry is configured to adjust exposure in the medical imaging device based on information regarding the brightness of the region classified as the biological tissue in the biological image.

10. The image processing device according to claim 1, wherein the processing circuitry is configured to adjust focus in the medical imaging device based on only information of the region classified as the biological tissue in the biological image.

11. The image processing device according to claim 1, wherein the processing circuitry is configured to correct blur in the biological image based on information regarding moving of the region classified as the biological tissue in the biological image.

12. The image processing device according to claim 1, wherein the processing circuitry is configured to:
process an image so as to hatch a position on the biological image corresponding to a type of a classified subject based on a classification result; and
control display of the biological image after processing the image.

13. The image processing device according to claim 12, wherein the processing circuitry is configured to:
specify a re-learning range requiring re-learning and specify a correct label indicating a correct subject on the displayed biological image, and
perform re-learning so as to classify a subject corresponding to the correct label in the re-learning range.

14. The image processing device according to claim 1, wherein
the biological image is an endoscopic image imaged by an endoscope.

15. An image processing method comprising:
smoothing a biological image generated by imaging an inside of a biological body including a biological tissue by a medical imaging device;
converting a pixel value of each pixel of the smoothed biological image into lightness, chromaticity, and brightness;
calculating, based on the brightness, a gradient direction and a gradient strength of the brightness of the each pixel in the smoothed image; and
classifying, based on the smoothed image, each subject included in each region in the biological image into the biological tissue or one other than the biological tissue, based on the lightness, the chromaticity, the gradient direction and the gradient strength, in units of blocks of a predetermined size in the biological image.

16. A medical imaging system comprising:
an image sensor configured to image an inside of a biological body including a biological tissue to obtain a biological image; and
processing circuitry configured to
smooth the obtained biological image,
convert a pixel value of each pixel of the smoothed biological image into lightness, chromaticity, and brightness,
calculate, based on the brightness, a gradient direction and a gradient strength of the brightness of the each pixel in the smoothed image, and
classify, based on the smoothed image, each subject included in each region in the biological image into the biological tissue or one other than the biological tissue, based on the lightness, the chromaticity, the gradient direction and the gradient strength, in units of blocks of a predetermined size in the biological image.

* * * * *